(12) United States Patent
Iizuka et al.

(10) Patent No.: US 8,266,964 B2
(45) Date of Patent: Sep. 18, 2012

(54) CALIBRATION OF AN ULTRASONIC FLAW DETECTOR AND QUALITY CONTROL AND PRODUCTION METHODS FOR A TUBULAR BODY

(75) Inventors: Yukinori Iizuka, Chiyoda-ku (JP);
Kazuhito Kenmochi, Chiyoda-ku (JP);
Hiroyasu Yokoyama, Chiyoda-ku (JP);
Tomohiro Inoue, Chiyoda-ku (JP);
Shigeto Sakashita, Chiyoda-ku (JP)

(73) Assignee: JFE Steel Corporation, Tokyo (JP)

( * ) Notice: Subject to any disclaimer, the term of this patent is extended or adjusted under 35 U.S.C. 154(b) by 387 days.

(21) Appl. No.: 12/528,975

(22) PCT Filed: May 18, 2007

(86) PCT No.: PCT/JP2007/060652
§ 371 (c)(1), (2), (4) Date: Aug. 27, 2009

(87) PCT Pub. No.: WO2008/105109
PCT Pub. Date: Sep. 4, 2008

(65) Prior Publication Data
US 2010/0107725 A1 May 6, 2010

(30) Foreign Application Priority Data
Feb. 28, 2007 (JP) .................................. 2007-048778

(51) Int. Cl.
*G01H 3/14* (2006.01)
*G01N 29/48* (2006.01)
*G01N 19/08* (2006.01)

(52) U.S. Cl. ................. 73/592; 73/587; 73/596; 73/598; 73/618

(58) Field of Classification Search .................... 73/587, 73/592, 596, 598, 615, 618, 619
See application file for complete search history.

(56) References Cited

U.S. PATENT DOCUMENTS
3,570,279 A * 3/1971 Davies ........................... 73/615
(Continued)

FOREIGN PATENT DOCUMENTS
JP 56143951 A 11/1981
(Continued)

OTHER PUBLICATIONS
International Search Report dated Aug. 7, 2007, application No. PCT/JP2007/060652.
(Continued)

*Primary Examiner* — David Rogers
(74) *Attorney, Agent, or Firm* — RatnerPrestia

(57) ABSTRACT

An ultrasonic flaw detection is performed to a welded portion 2 of a pipe body 1, a defect detection threshold value is determined based on the signal intensity difference between the total area of the defects existing in the region of an ultrasonic beam on a welded surface and an artificial defect, and a quality control of the pipe body is performed based on the defect detection threshold value. An equivalent defect diameter is determined from the defect density on the welded surface of the welded portion of the pipe body in a pipe axis direction and the area of the ultrasonic beam on the welded surface based on the total area of the defects existing in the region of the ultrasonic beam, and the defect detection threshold value is determined based on the equivalent defect diameter and the signal intensity difference of the artificial defect.

9 Claims, 27 Drawing Sheets

U.S. PATENT DOCUMENTS

| | | | |
|---|---|---|---|
| 4,393,711 A * | 7/1983 | Lapides | 73/592 |
| 4,406,167 A | 9/1983 | Maeda | |
| 4,577,507 A * | 3/1986 | Jestrich et al. | 73/640 |
| 4,742,713 A * | 5/1988 | Abe et al. | 73/620 |
| 4,803,638 A * | 2/1989 | Nottingham et al. | 702/36 |
| 6,399,939 B1 * | 6/2002 | Sundaresan et al. | 250/231.1 |
| 2003/0033881 A1 * | 2/2003 | Lam et al. | 73/627 |
| 2007/0261495 A1 * | 11/2007 | Van Der Ent et al. | 73/622 |
| 2009/0133786 A1 * | 5/2009 | Bewlay et al. | 148/670 |
| 2009/0150095 A1 * | 6/2009 | Wickersham, Jr. | 702/39 |

FOREIGN PATENT DOCUMENTS

| | | |
|---|---|---|
| JP | 61-111461 | 5/1983 |
| JP | 60-205356 | 10/1985 |
| JP | 63256851 A * | 10/1988 |
| JP | 59-202060 A | 1/1991 |
| JP | 04-274756 | 9/1992 |
| JP | 07-035729 | 2/1995 |
| JP | 11-183446 | 7/1999 |
| JP | 2000-221171 A | 8/2000 |
| JP | 3721827 B2 | 9/2000 |
| JP | 10-185881 A | 3/2001 |
| JP | 2007-874 A | 1/2007 |
| JP | 2007-163470 A | 6/2007 |

OTHER PUBLICATIONS

"Ultrasonic Flaw Inspection Series (II), Ultrasonic Flaw Inspection Method of Welded Steel Pipe" The Iron and Steel Institute of Japan, 28 to 31 pages, 1988.

* cited by examiner

FIG. 18
(a)
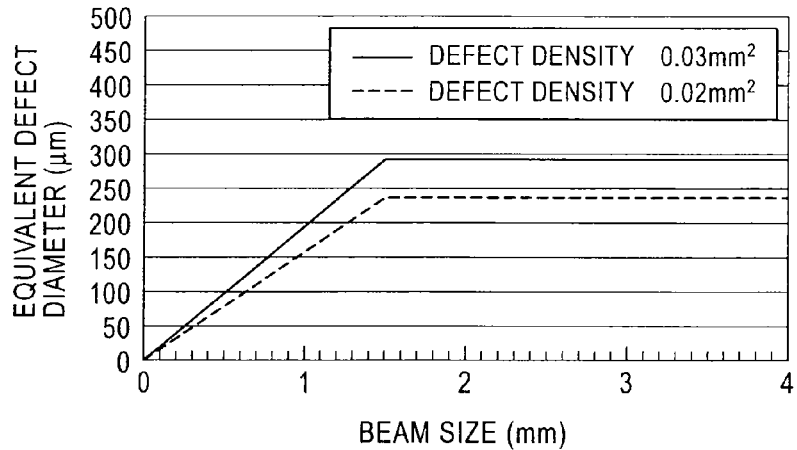
(b)
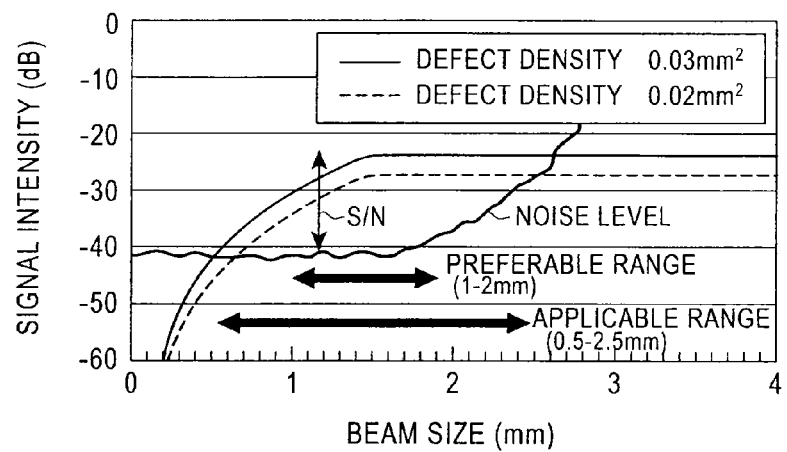
(c)
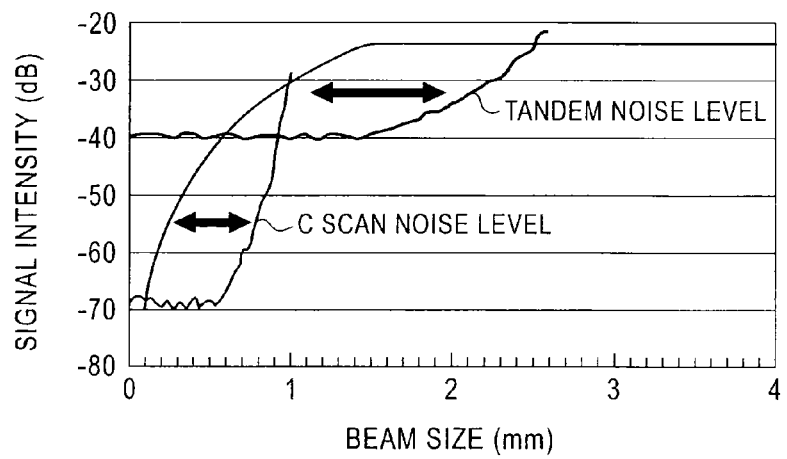

FIG. 20
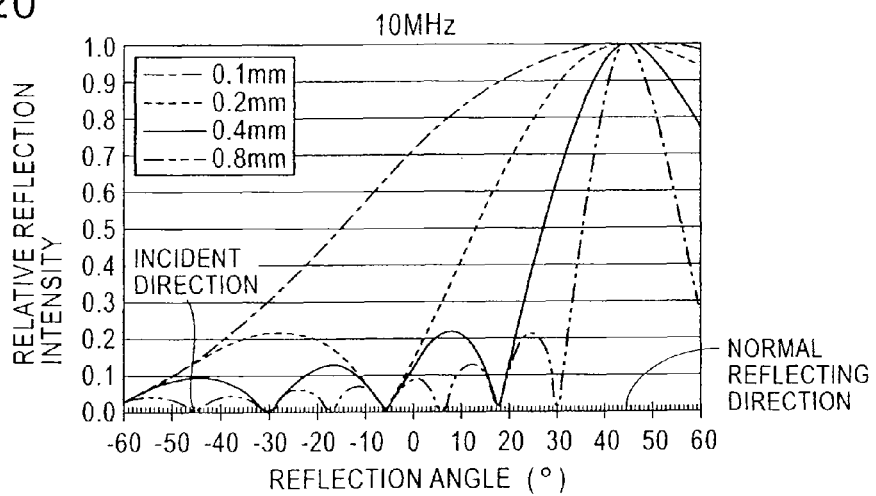
(a)
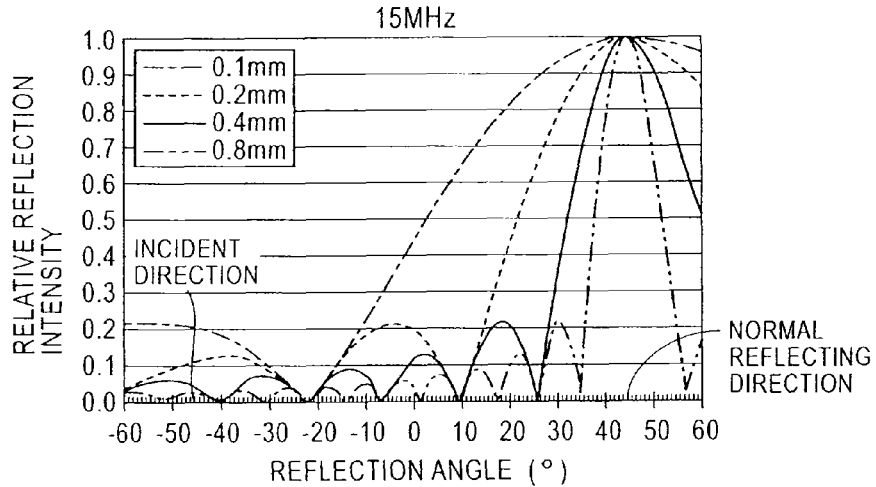
(b)
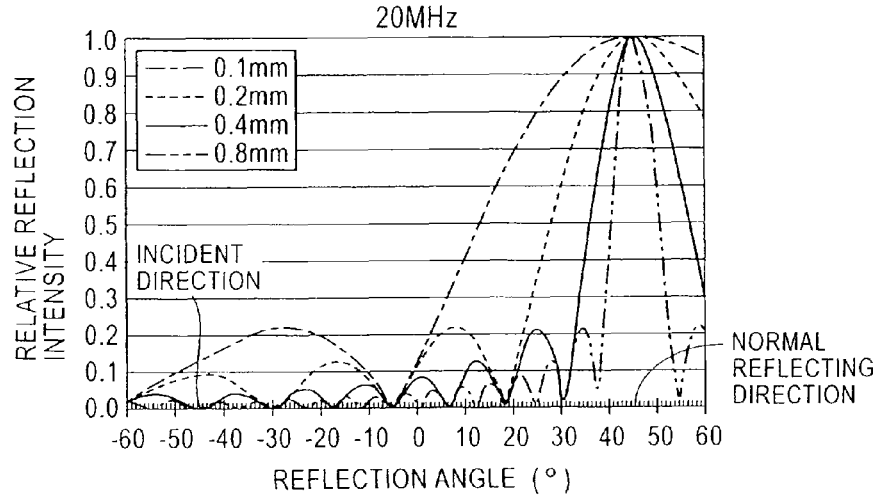
(c)

| SCAN LINE | TRANSDUCER No. | NUMBER OF TRANSDUCERS | DEFLECTION ANGLE | COLLECTING POINT DISTANCE |
|---|---|---|---|---|
| A | 17-22 | 6 | -6.0° | 31.7 mm |
| B | 71-90 | 20 | 0 | 103 mm |
| C | 124-155 | 32 | -6.0° | 177 mm |

CALIBRATION OF AN ULTRASONIC FLAW DETECTOR AND QUALITY CONTROL AND PRODUCTION METHODS FOR A TUBULAR BODY

This application is a U.S. National Phase Application of PCT International Application No. PCT/JP2007/060652, filed May 18, 2007, which claims priority to Japanese Patent Application No. 2007-048778, filed Feb. 28, 2007, the contents of each of these applications being incorporated by reference herein in their entirety.

TECHNICAL FIELD

The present invention relates to a calibration method of an ultrasonic flaw detection for accurately detecting a minute flaw penetrated to a welded portion of a welded steel pipe by an ultrasonic flaw detection, to a quality control method, and a manufacturing method of a pipe body.

BACKGROUND

In a welded steel pipe, since the quality of a welded portion is very important, an on-line flaw detection is generally performed to a welded portion by an ultrasonic angle beam technique in a manufacturing process. This method is such that an ultrasonic wave is caused to be obliquely incident on a inspection surface of a member to be inspected (hereinafter, referred to a material under test) to detect an inner and outer surface defect and an internal defect of the material under test from a reflected wave reflected on the defect. Ordinarily, in, for example, an electric resistance welded steel pipe, a reflection method of using an ultrasonic beam having a refraction angle of 45° at frequency of 5 MHz is used, and a defect having a size of the order of millimeter, for example, lack of penetration, burn-through, welding crack due to inclusions and the like is detected.

In contrast, recently, strict quality is required to a welded steel pipe, and it is required to detect a defect smaller than a conventional defect. For example, defects such as a cold joint defect and a minute penetrator are penetrated in a electric resistance welded steel pipe and defects such as a blow hole and the like are generated in a laser welded steel pipe, and these defects have a very small size of several tens of micron meters to several hundreds of micron meters. Further, there is a possibility that these defects are generated in any locations from an inner surface to an outer surface along a welding line, and the point on which an ultrasonic beam is incident may be different from a point to which it returns depending on a defect position. Since there are many cases in which defects can not be detected by conventionally practically used ultrasonic flaw detection methods due to these affects, a technology for detecting a defect more accurately is required.

The following conventional technologies are disclosed heretofore as a method of detecting a minute defect of a welded steel pipe. Patent Document 1 improves a detect resolution to a penetrator so that a point focus type probe having a frequency of 8 MHz or more can be used in a angle beam technique. Patent Document 2 improves a detect resolution by forming a focus beam by an array probe so that a blow hole can be detected by scanning from the inner surface side to the outer surface side of a welded portion by a sector scan.

Further, Patent Document 3 detects a cold joint defect formed of impurities as a group of minute FeO having a size of several micron meters or less by causing an ultrasonic wave having a frequency of 25 MHz or more to 500 MHz or less to be incident on a welded portion from the outer surface side of a pipe at an incident angle of 0° or more to 20° or less. Further, Patent Document 4 detects a blow hole of 0.1 mm or more by using a plurality of point focus type probes having a frequency of 20 MHz-80 MHz and disposing them so that a focusing position from just above a seam has a pitch of 3 mm or less.

However, the technologies disclosed above still have the problems described below. In the method of Patent Document 1, it has a problem in that since a focused ultrasonic beam has a narrow beam width, an equipment cost is increased because many channels are necessary to perform a flaw detection so that all the regions of a welded portion in a depth direction (wall thickness direction of a steel pipe) are not missed, and further a position adjustment and the like are very troublesome when a pipe size is changed. Further, when a defect shape is not a blow hole shape but a plane shape such as a penetrator and a cold joint defect and a defect is located inside of a wall thickness, it is difficult to detect the defect because a reflected wave travels in a direction different from an incident direction.

Since the method of Patent Document 2 can be performed using one array probe and setting can be made electronically when a size is changed, the former problem of Patent Document 1 can be solved. However, the latter problem thereof still remains unsolved.

When a defect shape is a plane shape as described above, since an upset is applied to, for example, the seamed portion of a electric resistance welded steel pipe, a defect has a very thin width of 100 μm or less when it is viewed from just above a seam. Accordingly, even the methods of Patent Documents 3 and 4 are difficult to detect the defect actually in many cases because a reflected wave from the defect is very weak. Further, a problem arises in that since an area of about 1-2 mm in the vicinity of a surface echo is made to a dead zone by the reverberation of the surface echo, when a defect is positioned in the vicinity of an outer surface, the defect cannot be detected.

As described above, it is difficult for the technologies, which detect a minute defect of about several hundreds of micron meters generated in the welded portion of a welded steel pipe in a pipe axis direction, to cope with the recently required strict quality control, and thus there is desired to develop a technology for solving these problems.

[Patent Document 1] Japanese Unexamined Patent Application Publication No. 60-205356
[Patent Document 2] Japanese Unexamined Patent Application Publication No. 11-183446
[Patent Document 3] Japanese Unexamined Patent Application Publication No. 61-111461
[Patent Document 4] Japanese Unexamined Patent Application Publication No. 7-35729
[Patent Document 5] Japanese Unexamined Patent Application Publication No. 4-274756
[Non Patent Document 1] "Ultrasonic Flaw Inspection Series (II), Ultrasonic Flaw Inspection Method of Welded Steel Pipe" The Iron and Steel Institute of Japan, 28 to 31 pages, 1988

SUMMARY

The present invention, which was made in view of the above circumstances, makes it possible to accurately detect a minute defect positioned inside of the wall thickness of a welded portion of a steel pipe even if the steel pipe is a electric resistance welded steel pipe to which a strict quality control is required and to perform the quality control based on a result of the detection. As a result of a diligent research, the inventors have found a novel and useful knowledge that the existence of defects such as penetrators and the like remaining in a welded portion affects the mechanical characteristics of the welded surface of a electric resistance welded steel pipe in a pipe axis direction, and although the size of a simple defect is so small that it does not cause any problem, the existing amount of the defects (the number of the defects in a certain area) greatly affects the mechanical characteristics of the welded portion.

At first, the inventors considered that what greatly affected the mechanical characteristics of the welded portion of a electric resistance welded steel pipe was the size of a penetrator and that the mechanical characteristics were good when a penetrator existing in the welded portion was small to a certain degree. As a result of examination of a flaw detection method of these defects, the inventors conceived a technology for detecting these defects by making the width of an ultrasonic beam to be transmitted and received smaller than that of a conventional ultrasonic flaw detection method. However, when a result of evaluation of presence or absence of a penetrator evaluated using the ultrasonic flaw detection technology employing a reduced beam width was compared with mechanical characteristics, the result was thoroughly different from an assumed result. That is, there was obtained such a result that even if a penetrator was detected, the mechanical characteristics were good and even if no penetrator was detected, the mechanical characteristics were bad on the contrary. Thereafter, as a result of more detailed examination, the inventors have found a very useful knowledge that a penetrator, in which minute defects of several micron meters scatter in a wide range, correlates with mechanical characteristics. Then, the inventors have developed an ultrasonic flaw detection technology for detecting the penetrator.

Here, a type of a penetrator will be explained using FIG. 1. At first, it was considered that a type of a minute defect such as a penetrator and the like was originally composed of oxides (mainly Si—Mn) of several micron meters closely gathering (aggregating) in a region having a size of several tens to several hundreds of micron meters and the oxides were seemingly recognized as one defect (in the description, the penetrator was also referred to as an aggregating type penetrator). However, it was found by the investigation of the inventors that there existed a penetrator (in the description, also referred to as a scattering type penetrator) of a type in which a lot of oxides of several micron meters were distributed (scattered) in a wide region as shown in 3b. The scattering type penetrator was not obviously detected by the conventional detection methods and was not made apparent because it had a thin density and thus it was very difficult to observe the cross section thereof. However, as the result of the detailed investigation of the inventors, it was found for the first time that the scattering type penetrator was a very important target to be detected to evaluate the mechanical characteristics, in particular to evaluate a level (level required by the strict quality control) in which the characteristics were good. The inventors have conceived an invention that provides methods for performing a quality control of a welded portion of a electric resistance welded steel pipe based on the knowledge.

FIG. 2 shows a result obtained by performing a Charpy impact test to Charpy test pieces cut out from a sample pipe. As a result of the Charpy impact test, samples A (three pieces) exhibit good mechanical characteristics of absorbed energy of 400 J or more, whereas samples B (three pieces) exhibit absorbed energy of about 200 J.

Then, in the vicinity of each of the portions where these Charpy test pieces were cut out, a sample S was obtained by cutting out (slicing) the welded portion 2 of a welded surface of a electric resistance welded steel pipe 1 in a pipe axis direction at a position 4 mm away from the welded surface in a peripheral direction as shown in FIG. 3, a flaw detection was performed to the welded portion by a C-scan method using a focusing type ultrasonic probe 50 to a cut-out surface, and a result of the flaw detection was compared with the result of Charpy impact test. First, the inventors considered that the existence of the aggregating type penetrator, which closely gathered in the region of several tens to several hundreds of micron meters described above, affected the mechanical characteristics of the welded portion and performed the flaw detection using the focusing type ultrasonic probe 50 having a frequency of 50 MHz and reducing a beam width to 100 μm. FIG. 4 shows a result of the search. FIG. 4(a) shows the C-scan data of the samples A, wherein a lateral axis shows a pipe axis direction, a vertical axis shows a thickness direction, and signal intensity is shown by a dark and light coloring (large amount of the signal intensity is more white). FIG. 4(b) shows the maximum values of the signal intensity in a thickness direction at the same positions in the pipe axis direction as to the data of (a), wherein a lateral axis shows positions in the pipe axis direction, and a vertical axis shows the maximum values of the signal intensity plotted along it. Likewise, FIGS. 4(c) and 4(d) show a result of the ultrasonic flaw detection as to the samples B. Note that in results of (b), (d), vertical axes show the values of defect diameters estimated from the maximum values of the signal intensity in the thickness direction. In the samples. A, a lot of scattering defect instructions (corresponding to the aggregating type penetrator described above) of the signal intensity corresponding to a defect diameter of 50 μm or more were observed, whereas, in the samples B, the scattering defect instructions were not almost observed. The result showed that even if aggregating type penetrators existed, the mechanical characteristics were good and an absorbed energy was low in the samples in which penetrators were not almost detect, which was a result entirely contrary to the result assumed by the inventors first.

Next, the inventors performed measurements by variously changing measurement conditions. In the measurements, when a beam width was increased (specifically, increased from 100 μm to 250 μm), it was found that a signal, which could not be confirmed up to that time could be obtained. FIG. 5 shows a result of the measurement. As to the samples A whose mechanical characteristics were good in the Charpy impact test, high defect signals having a signal level of a defect diameter of about 100 μm were confirmed in several portions with a signal level corresponding to a defect diameter of about 25 μm which was greatly smaller than a defect diameter of 40 μm as a base likewise FIG. 4. In contrast, as to the samples B, signals (in an image of the figure, pale and dilute instructions) showing signal intensity corresponding to a defect diameter of about 40 μm were confirmed throughout the entire length in the pipe axis direction, although no defect signals having a high signal level did not existed likewise FIG. 4. Based on the result described above, the inventors have reached a knowledge that defects, which are distributed widely although the signal level thereof corresponds to the defect diameter of about 40 μm and is not so high, greatly affect the mechanical characteristics of a welded portion.

Further, when the cross sections of the samples B were investigated by an electronic microscope, it was confirmed that fine oxides (minute penetrators) each having a size of 5 μm to 20 μm sparsely existed in the defect instructing portions observed in the samples B, and this was supported by a result of a C-scan.

Here, a reason why a pale echo band was detected when the ultrasonic beam width was increased will be examined. When a state in which minute reflection sources uniformly scatters in a wide range is considered, only a small number of the minute reflection sources are included in a beam when the beam has a narrow beam width as shown in FIG. 6. Therefore, the ratio of the total area of defects to a beam area is low with a result that a reflection echo is weakened. In contrast, when the beam width is increased, many minute reflection sources are included in a beam and thus the ratio of the total area of defects to a beam area is made high. Therefore, even if respective echoes are weak, they are made strong by being cumulated with a result that a detected signal level is made high.

A new knowledge has been derived from the above results in that penetrators (scattering type penetrators), which exhibit a state in which they are distributed in a wide region although each of them has a very small defect diameter, also affect the mechanical characteristics of a welded portion and a beam width has a preferable range to accurately evaluate the penetrators, and a quality control can be performed based on a result detected by the preferable condition.

It has been found based on the knowledge and the analysis of the inventors that although sensitivity is insufficient in the degree of beam focusing of a conventional technology level, the penetrators cannot be detected when a beam is excessively focused. According to aspects of the present invention, there is a preferable range in an ultrasonic beam width to detect a penetrator which greatly affects the quality of a welded portion and it is possible to securely perform a quality control based on a calibration method of a determination level (threshold value) for evaluating the quality of a welded portion of a electric resistance welded steel pipe, the calibration method being derived from the result of detection obtained by a beam width having the preferable range.

Note that since an array probe is used in embodiments of the present invention. Thus, it is sufficient to consider that a beam width, which is referred to in the description, is an effective value obtained from a square root of a beam area. However, there may be a case that focusing in the pipe axis direction is not necessary such as a case that penetrators are continuous in the pipe axis direction, it may be considered that the beam width is a beam width in a pipe wall thickness direction.

The following means are specifically provided to solve the above problems.

(1) A calibration method of an ultrasonic flaw detection is characterized in that, when the ultrasonic flaw detection is performed to a welded portion of a pipe body, a defect detection threshold value is determined based on the signal intensity difference between the total area of the defects existing in the region of an ultrasonic beam on a welded surface and an artificial defect.

(2) The calibration method of the ultrasonic flaw detection according to (1) is characterized in that the total area of the defect is determined from the defect density, which is determined from a desired quality level, on a welded surface of a welded portion of a pipe body in a pipe axis direction and the area of the ultrasonic beam on the welded surface.

(3) The calibration method of the ultrasonic flaw detection according to (2) is characterized in that the relation between the defect density and the quality level is previously determined by a Charpy impact test.

(4) The calibration method of the ultrasonic flaw detection according to (2) is characterized in that the signal intensity difference between the artificial defect and the equivalent defect is determined based on the relative relation of acoustic reflectivity.

(5) A quality control method of a pipe body for performing a quality control by performing an ultrasonic flaw detection to a welded portion of the pipe body in at least a pipe axis direction is characterized by comprising a step of determining a defect detection threshold value by the calibration method according to any one of (1) to (4).

(6) The quality control method of the pipe body according to (5) is characterized by comprising a wave transmission unit for transmitting an ultrasonic wave to a welded surface of a welded portion of the pipe body in a pipe axis direction; and a wave reception unit for partly or entirely receiving a reflected wave on the welded surface, wherein the wave transmission unit and the wave reception unit perform the ultrasonic flaw detection using an ultrasonic flaw detection apparatus comprising a transmission/reception unit composed of different transducer groups on one, two, or more array probes disposed in a pipe peripheral direction.

(7) The quality control method of the pipe body according to (6) is characterized in that the wave transmission unit transmits ultrasonic waves to the welded surface of the welded portion of the pipe body in the pipe axis direction and to an inner surface of the pipe body so that the ultrasonic waves are incident thereon in the range of from 33.2° to 56.8°, respectively, and the wave reception unit partly or entirely receives a reflected wave reflected in the range of from −12° to 16° with respect to a normal reflection direction on the welded surface.

(8) The quality control method of the pipe body according to (7) is characterized in that the beam width of the ultrasonic wave on the welded surface is set within the range of from 0.5 mm to 2.5 mm.

(9) A manufacturing method of a pipe body is characterized by comprising a manufacturing step of manufacturing a pipe body, and a quality control step of performing a quality control of the pipe body manufactured at the manufacturing step by the quality control method of the pipe body according to any of (5) to (8).

Since penetrators can be accurately determined as defects by the present invention, a welding process can be improved so that minute defects, which affect the mechanical characteristics of a welded portion of a welded steel pipe, are not generated and pipe with weld defects can be selected at the manufacturing process so that the pipe of imperfection is not shipped. As a result, since the quality of the welded steel pipe can be dramatically increased, it can be used in a use condition which is more severe that a conventional use condition.

BRIEF DESCRIPTION OF THE DRAWINGS

FIG. 18 is a view showing the relation between a beam size and signal intensity.

FIG. 20 is a view explaining the relation between a defect size and reflection directivity.

Figure 1:
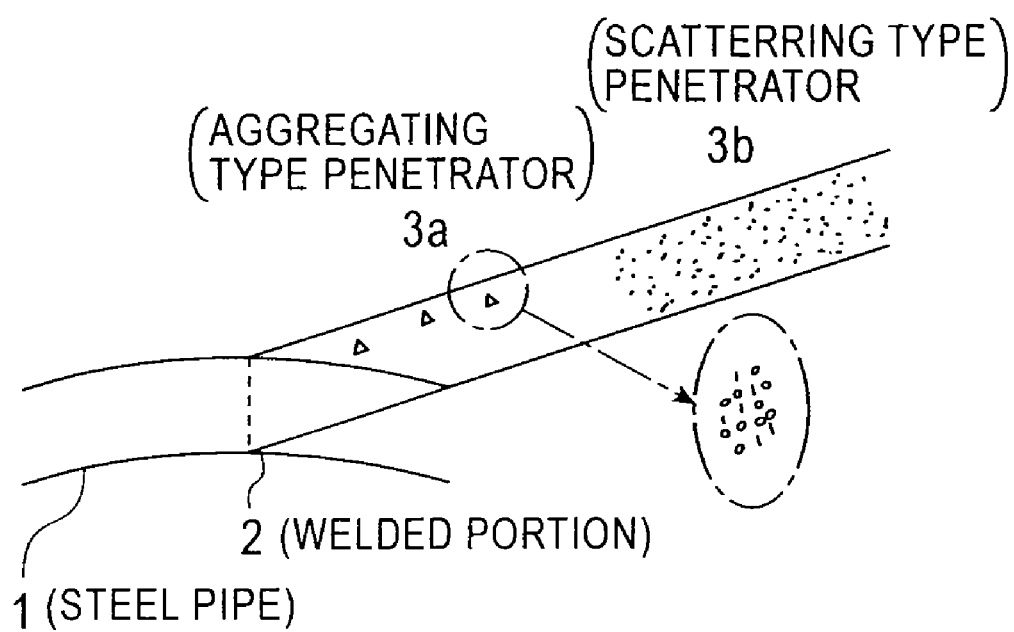
FIG. 1 is a perspective view showing a type of minute penetrators found by the investigation of the inventors.
Figure 2:
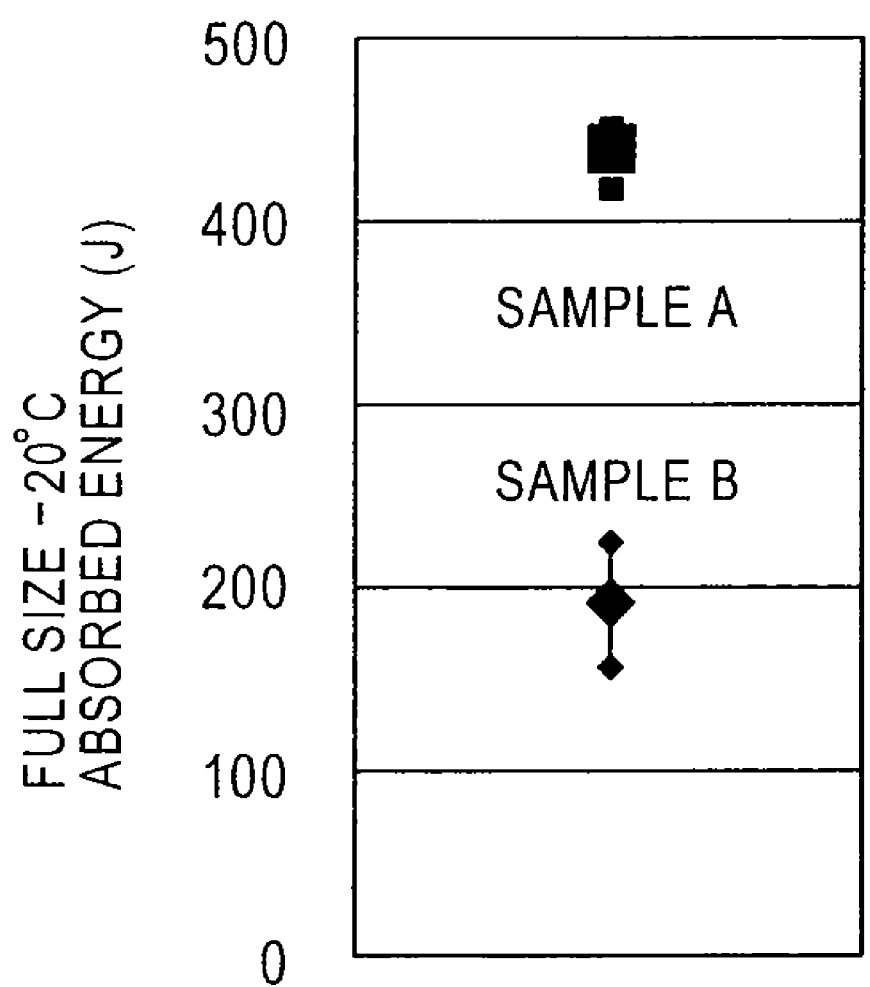
FIG. 2 is a view showing a result of samples subjected to a Charpy impact test.

| Reference numerals in the figures are shown below. | |
| --- | --- |
| 1 | steel pipe |
| 2 | welded portion |
| 3 | defect |
| 4 | water |
| 5 | linear array probe |
| 6 | transducer group for transmitting of wave |
| 7 | transducer group for receiving of wave |
| 8 | transmitted beam |
| 9 | received beam |
| 10 | flaw detection condition calculation unit |
| 11 | delay time setting unit |
| 12 | pulser |
| 13 | transducer of linear array probe |
| 14 | receiving amplifier |
| 15 | delay time setting unit |
| 16 | synthesization process unit |
| 17 | gate evaluation unit |
| 30 | material under test size input unit |
| 31 | array probe storage unit |
| 32 | aperture width controller |

| Reference numerals in the figures are shown below. | |
| --- | --- |
| 33 | gate position storage unit |
| 34 | array transmission law storage unit |
| 35 | array reception law storage unit |
| 36 | array transmission unit |
| 37 | array reception unit |
| 38 | gate unit |
| 39 | detection threshold value input unit |
| 40 | defect determination unit |
| 70 | sensitivity calibration unit |

DETAILED DESCRIPTION

Figure 7:
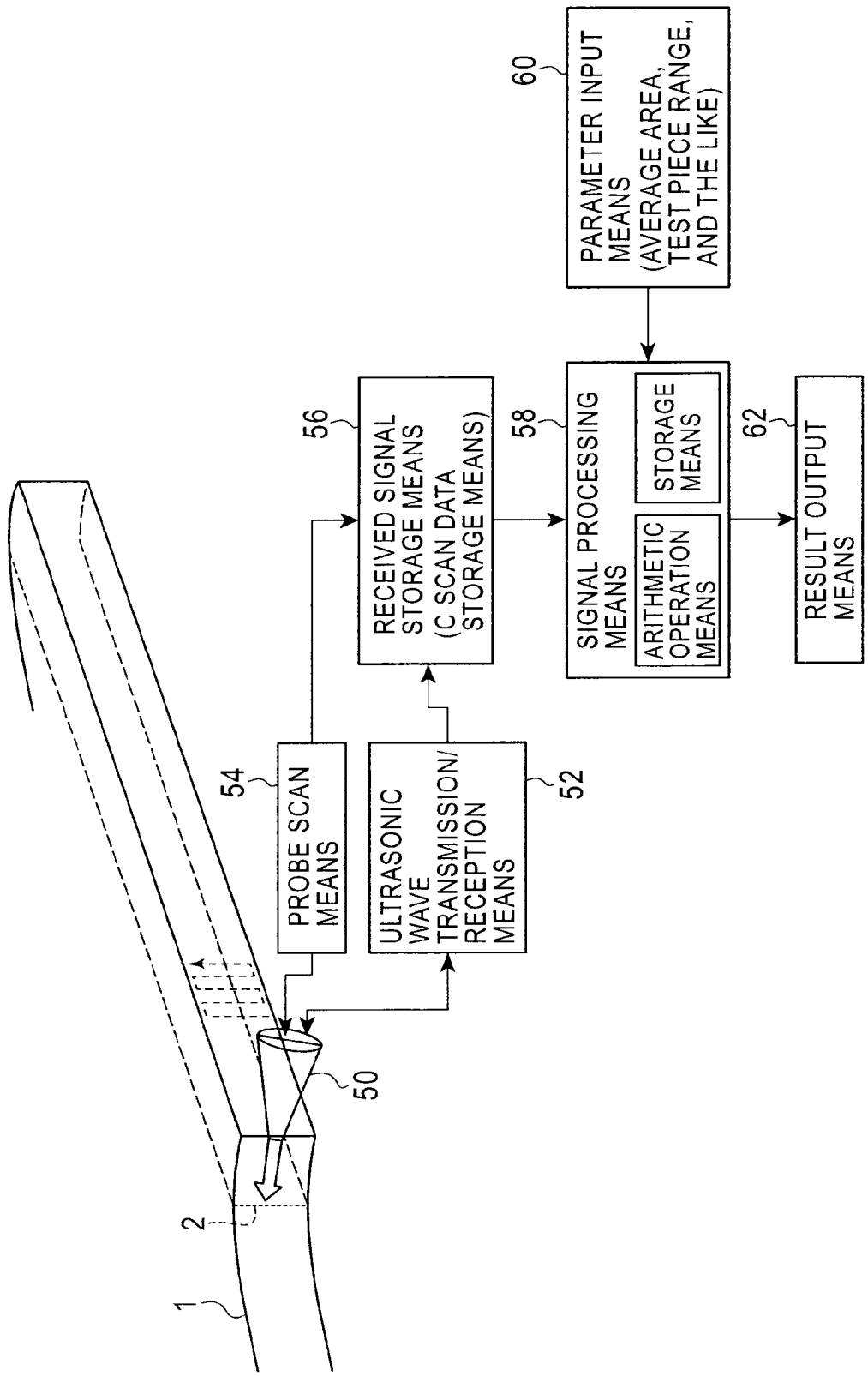
FIG. 7 is a view showing an example of a function arrangement for performing an experiment for comparing the C-scan with the Charpy impact test.

First, conditions, by which a scattering type penetrator, in which minute defects affecting the mechanical characteristics of a welded portion were distributed in a wide range, could be detected, were set, a flaw detection was performed by a C-scan method, and the conditions were compared with a result of the flaw detection and evaluated. FIG. 7 shows an example of an arrangement for performing the evaluation. The example is composed of a probe 50 for performing an ultrasonic flaw detection by transmitting and receiving an ultrasonic wave to and from a cut-out welded surface, an ultrasonic wave transmission/reception means 52 for controlling the transmission and reception of an ultrasonic wave in the probe 50, a probe scan means 54 for sequentially scanning the probe 50 in a pipe axis direction and in a pipe thickness direction to subject a welded surface of the cut-out sample to a C-scan, a received signal storage means 56 for storing C-scan data, a signal processing means 58 for subjecting the C-scan data to an arithmetic processing, a parameter input means 60 for inputting parameters necessary to the arithmetic processing, and a result output means 62.

Here, the received signal storage means 56 is arranged such that it stores the signal received by the ultrasonic wave probe 50 after the signal is caused to correspond to a position at which the welded surface is scanned by the probe scan means 54. The received signal storage means 56 is, for example, a memory (two-dimensional memory) capable of storing received signal intensity with respect to the pipe axis direction and the pipe thickness direction and is a so-called C-scan data memory means having a function of storing the C-scan data.

The signal processing means 58 inputs parameters necessary to the arithmetic processing to be described later to the data of the memory by the parameter input means 60 and calculates index values having correlation with the mechanical characteristics, and the index values are displayed by images or printed to the result output means 62 such as a CRT, a liquid crystal monitor, a printer, and the like.

Figure 3:
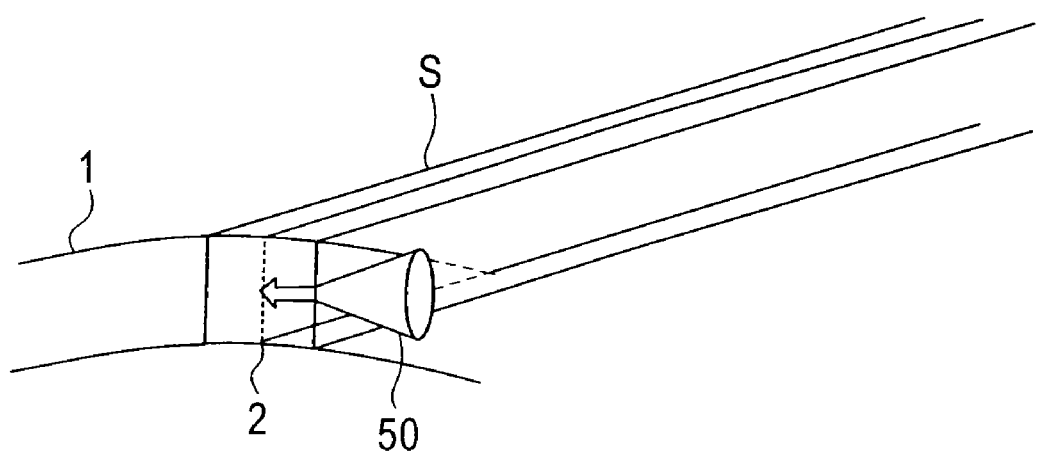
FIG. 3 is a perspective view showing a C-scan method of a seam sliced member for explaining a principle of the present invention.
Figure 4:
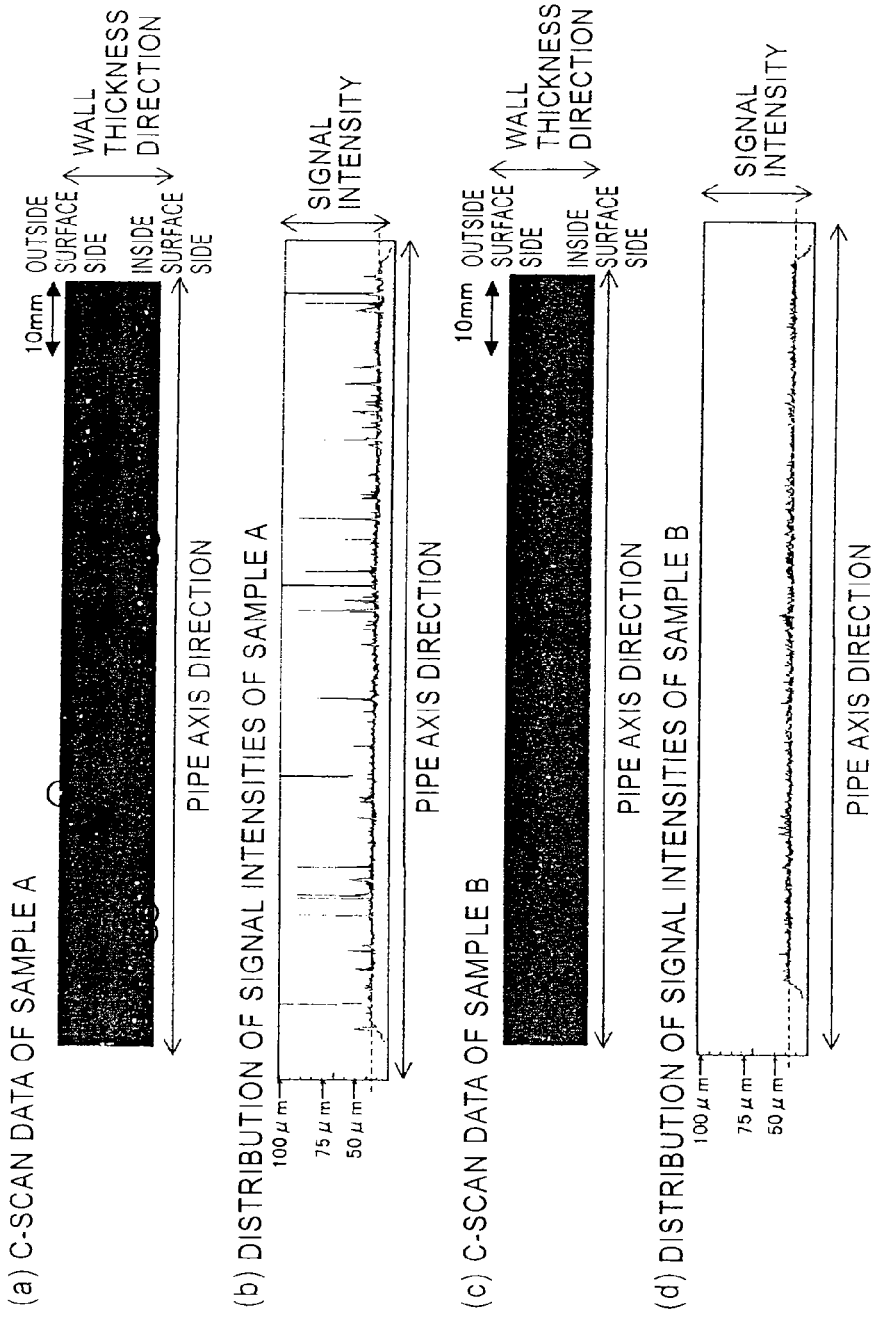
FIG. 4 is a view showing a result of the C-scan performed at 50 MHz with a beam diameter set to 100 μm likewise.
Figure 5:
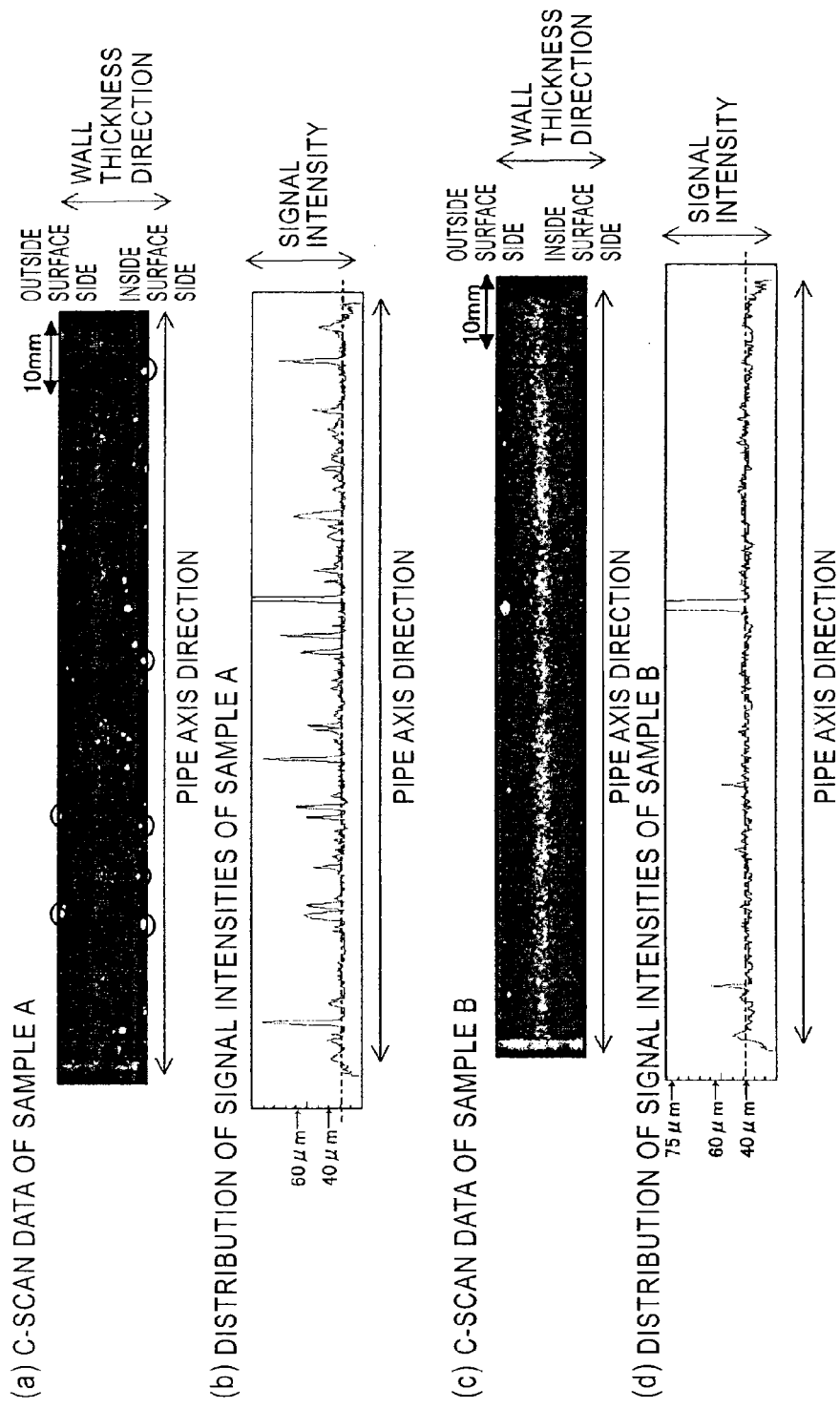
FIG. 5 is a view showing a result of the C-scan performed at 50 MHz with a beam diameter set to 250 μm likewise.

This arrangement was used, and specifically, a sample, which was cut out (sliced) at a position 8 mm away from a welded surface (seam) as shown in FIG. 3, was made, and the point focusing type probe 50 having a frequency of 20 MHz was used from an end surface, and a beam width on the welded surface was set to 440 μm. The beam width was selected to 440 μm because this size was within a preferable range when a scattering type penetrator, in which minute defects were distributed in a wide region (within the range of, for example, 1.5×1.5 mm, 2×2 mm) was detected in the C-scan as described later. Further, in the C-scan, the welded surface was measured in the thickness direction and in the pipe axis direction. Note that, at the time, the sensitivity of the C-scan was adjusted such that the echo height of a flat-bottomed hole of 125 μmφ was set to 100%.

Next, the mechanical characteristics were determined at the same location as that where the C-scan was performed. Specifically, a sample of 10 mm in a longer direction×about 10 mm in the thickness direction was cut out and arranged as a Charpy test pieces by pressure welding a joint thereto so that a notch portion is not thermally affected, a Charpy impact test was performed to the test piece at −40° C., and Charpy absorbed energy was measured at a tested portion.

Then, a value acting as the index value of the mechanical characteristics was calculated from the measured data (echo height of an ultrasonic wave) detected by the ultrasonic wave, and whether or not there is a correlation between the value and the Charpy absorbed energy was evaluated.

Figure 8:
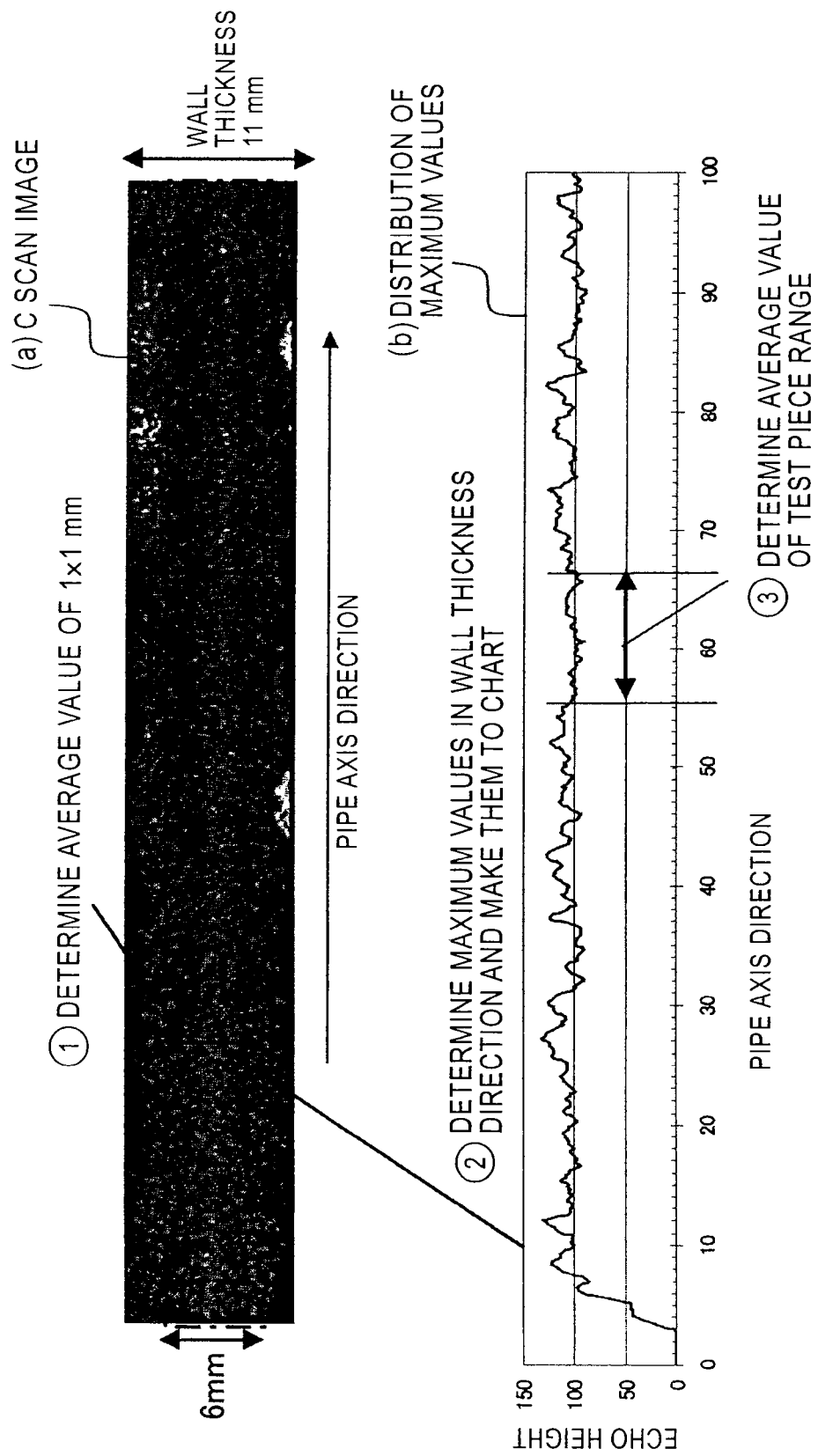
FIG. 8 is a view showing a C-scan data process likewise.

FIG. 8 shows an example of an arithmetic processing method of the index value to be compared with the mechanical characteristics.

FIG. 8(*a*) shows an image obtained from the C-scan, wherein a vertical axis shows a wall thickness direction, and a lateral axis shows a pipe axis direction. It is shown that a portion having bright tone has a high ultrasonic wave echo and thus has a high defect density and that a portion having dark tone has a low ultrasonic wave echo and thus has a low defect density. In this data, it can be found that a lot of minute defects are distributed in the range of 6 mm in the vicinity of a central portion in a wall thickness of 11 mm.

The data was subjected to the following processes, and an index value was determined:

i) An average value was calculated within the range of a predetermined region (here, set to, for example, 1 mm×1 mm) about respective data, and average value data was created;

ii) A maximum value distribution data was calculated by determining maximum values in the wall thickness direction at the same position in the pipe axis direction with respect to the average data, the maximum value distribution data corresponding to FIG. 8(*b*); and iii) An average value within the range in which the Charpy test piece was cut out was calculated as to the maximum value distribution data, and the value was used as an index to be compared with a result of the Charpy test.

Note that, in the above processes, since defects are concentratedly distributed in the vicinity of the center of a wall thickness portion, the processes were performed within the range of a central portion of 6 mm as to the wall thickness direction.

Figure 9:
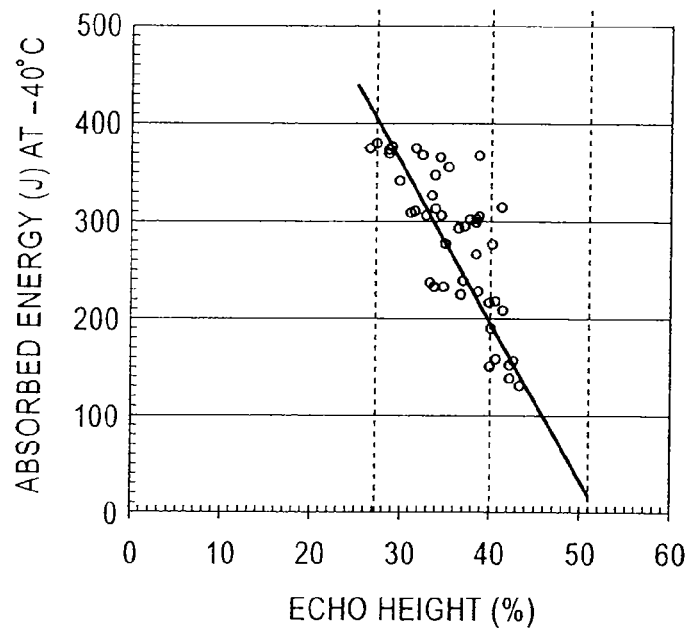
FIG. 9 is a view showing the relation between an echo height and absorbed energy likewise.

FIG. 9 shows the relation between the index values, which are determined from the C-scan by performing these processes to a lot of samples at a plurality of positions, and a result of the Charpy test. FIG. 9 shows data, wherein a lateral axis shows the index value (shown by echo height), and the results of the Charpy test are plotted along a vertical axis.

As can be found from the mentioned above, since FIG. 9 shows a tendency that a smaller index value (echo height) more improves the mechanical characteristics, it can be found that the quality of a welded portion can be evaluated by the index value (echo height).

Figure 6:
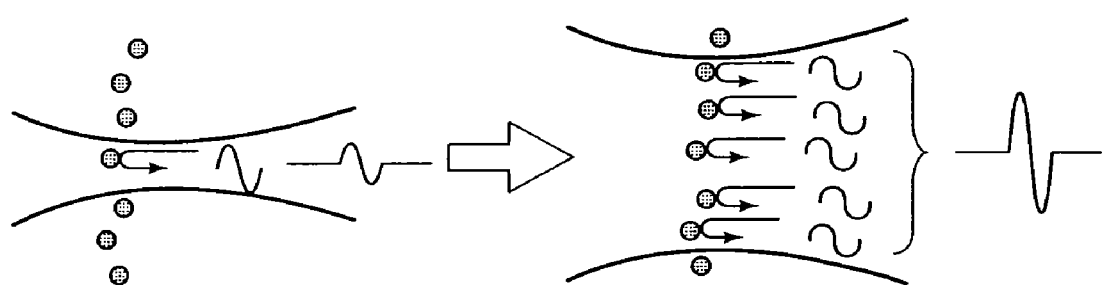
FIG. 6 is a detection image view when reflection sources scatter likewise.

Although it is generally considered that an echo height is caused by a defect area, since a target to be detected by embodiments of the present invention is a scattering type penetrator in which minute defects are distributed in a wide range, the above consideration cannot be easily applied to the present invention as it is. Then, the inventors have found a knowledge that an echo height detected in a scattering type penetrator is not a signal obtained by the reflection from one minute defect but a signal obtained by cumulating the reflections from all the defects existing in an ultrasonic beam (here, beam width is 440 μm) as shown in the schematic view of FIG. 6. That is, the inventors have considered that an echo height has a correlation with the total area obtained by totaling the defect areas existing in an ultrasonic beam and that when, for example, respective defect areas are the same, a higher defect density more increases the echo height. Thus, the inventors derived a value called an equivalent defect diameter which permitted the total area of defects existing in an ultrasonic beam to be seemingly treated as one defect area.

Figure 10:
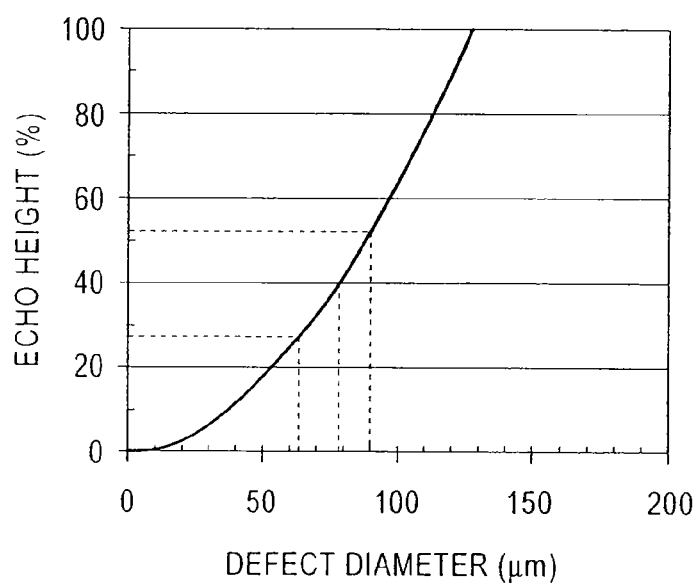
FIG. 10 is a view showing the correlation between a defect diameter and an echo height likewise.

For example, since an echo height is proportional to a defect area in the above measurement condition of the C-scan, when the relation between the echo height and an equivalent defect is calculated, a result of the calculation is as shown in FIG. 10, from which it is possible to cause the equivalent defect to correspond to a mechanical characteristic value. From the described above, a combination of FIG. 9 and FIG. 10 permits to perform a sensitivity calibration using an artificial defect whose size is previously known even in a scattering type penetrator. When, for example, sensitivity is adjusted so that the echo height of the artificial defect acts as a reference value, the echo height of the equivalent defect diameter can be determined from the correlation between the equivalent defect diameter corresponding to required mechanical characteristics and the artificial defect using the reference value determined in the artificial defect as a reference, and the echo height can be determined as a threshold value for evaluating the mechanical characteristics of a welded portion.

Although a result of the investigation performed by subjecting the seam sliced samples to the C-scan is explained above, since the same investigation is possible even if the samples are in the state of steel pipes, this will be explained below.

Figure 11:
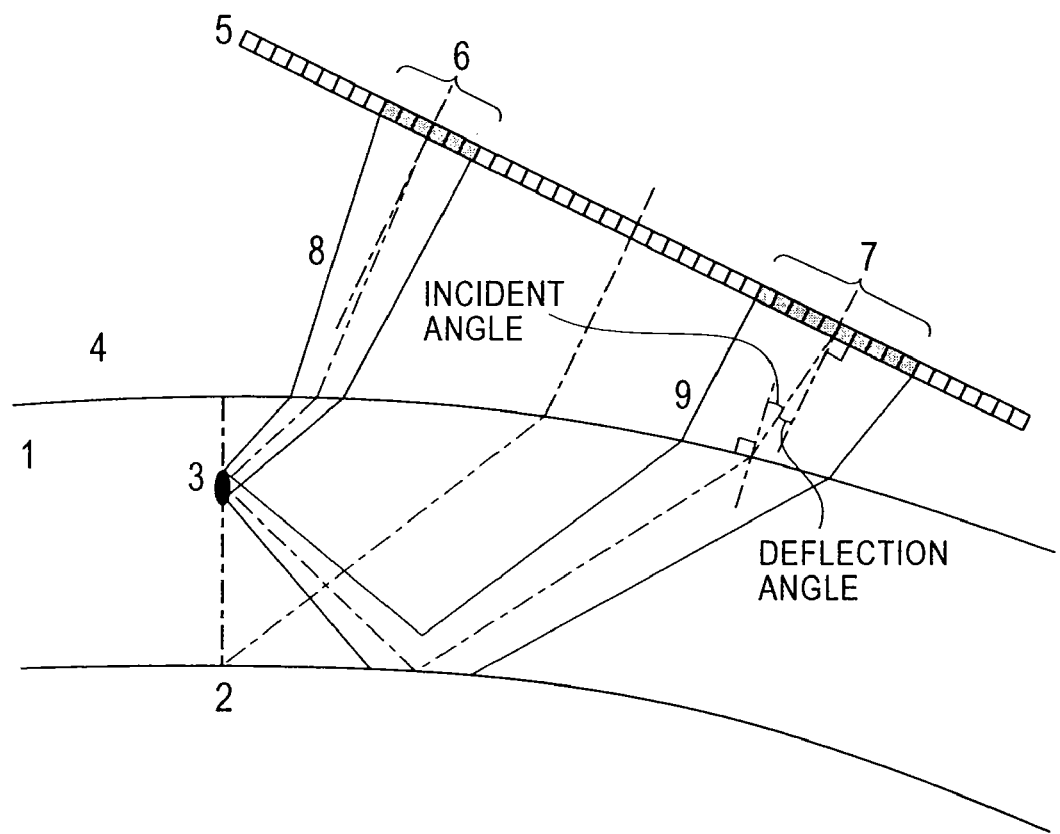
FIG. 11 is a view explaining a principle of a tandem method.

FIG. 11 is a view explaining a principle of a tandem flaw detection as one of flaw detections for detecting a scattering type penetration in a steel pipe itself. In FIG. 11, 1 denotes a steel pipe as a material under test, 2 denotes a welded portion, 3 denotes a defect inside of a wall thickness portion, 4 denotes water in which an ultrasonic wave is transmitted, 5 denotes a linear array probe, 6 denotes a wave transmission transducer group, 7 denotes a wave reception transducer group, 8 denotes a transmitted beam, and 9 denotes a portion showing an ultrasonic wave traveling from a defect to the wave reception transducer group (hereinafter, also referred to as a received beam), respectively. Further, a line drawn in the intermediate portion of the transmitted beam 8 and the received beam 9 shows a scan line of them.

The linear array probe 5 has such a size that the ultrasonic wave, which is transmitted from a transducer group positioned on a side near to the welded portion 2 (left side direction in FIG. 11), is directly incident from the outer surface of the steel pipe of the welded portion and the ultrasonic wave, which is transmitted from a transducer group positioned far from the welded portion, is incident on the outer surface of the steel pipe of the welded portion after it is reflected once on the inside surface of the steel pipe. Then, the linear array probe 5 is disposed to have an incident angle to the outer peripheral surface of the steel pipe so that a transmitted beam emitted vertically from a center enters from the outer surface side of the steel pipe as a shear wave having a refraction angle of 45° and is incident on the edge on the inner surface side of the steel pipe of the welded portion (referred to as 0.5 skip).

The delay times of respective transducers are set such that the ultrasonic beam from the wave transmission transducer group is slightly deflected to the center axis side of the array probe in conformity with the outside diameter of the steel pipe so that it has a refraction angle of 45° as well as is focused at a position traversing the welded portion 2. Likewise, the wave reception transducer group 7 is selected such that it can receive the reflection echo from the defect 3 as a reflected wave reflected once on the inner surface side, and the delay times of respective transducers are set such that an ultrasonic beam slightly deflects the directivity thereof to the center axis side of the array probe in conformity with the outside diameter of the steel pipe so that it has a refraction angle of 45° as well as is focused at a position traversing the welded portion 2. The refraction angle is not limited to 45° and can be applied to the range of about 30°-70° in which a flaw detection can be preformed by a shear wave. However, when the angle dependency of a acoustic reflectivity when the shear wave is reflected on the defect and the inner surface is taken into consideration, the refraction angle is preferably set to the range of about 35°-55° in which total reflection is achieved. Further, the refraction angle may be set to the range of 40°-50° in consideration of safety.

As described above, since the positions and the numbers of the transducer groups and the refraction angles of a transmitted beam and a received beam are set so that focusing is performed in conformity with the position of the welded portion and the positional relation of the transducer groups are set so that the reflected wave from the defect can be received, it is possible to detect the reflection from a minute defect in an inner wall thickness portion.

Figure 12:
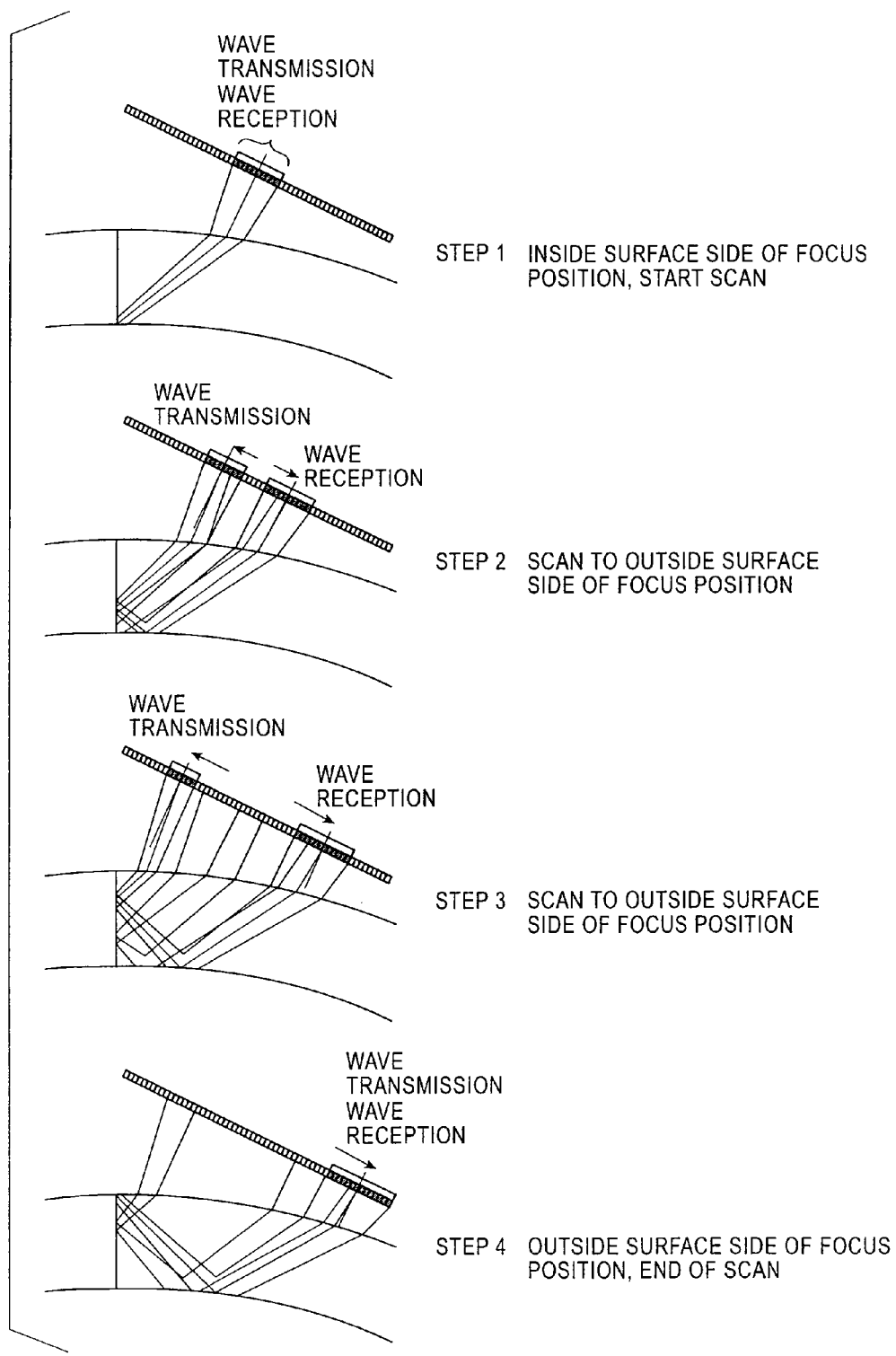
FIG. 12 is a view showing an example of a procedure of scan in the tandem method.

Next, FIG. 12 shows an example of a procedure for scanning the welded portion from the inner surface to the outer surface of the steel pipe. First, at step 1 showing start of scan, a flaw detection of 0.5 skip is performed using a transducer group in the vicinity of the linear array probe with a focusing position (the focus position) set on the inner surface side of the steel pipe of the welded portion. At the time, wave transmission and wave reception are performed by the same transducer group. Next, at step 2, the wave transmission transducer group is offset to the welded portion side as well as the wave reception transducer group is offset to a side far from the welded portion, and the focus position is set slightly above the inner surface side of the steel pipe of the welded portion (outer surface side of the steel pipe), thereby a flaw detection is performed to the inner wall thickness portion slightly above the inner surface side of the steel pipe of the welded portion (outer surface side of the steel pipe) by the tandem flaw detection.

Subsequently, at step 3, the wave transmission transducer group is offset to the welded portion side, the wave reception transducer group is offset to a side opposite to the welded portion, and a flaw detection is performed by shifting a position to be searched to the outer surface side of the steel pipe. Although only steps 2 and 3 are shown in the drawing, actually, the number of the transducer groups to be offset is determined so that ultrasonic beams partly overlap in order to that the inspection is neither omitted (performed) nor overlapped in consideration of the focus size of the ultrasonic beam (beam size at the focus position). Finally, at step 4 showing end of scan, a flaw detection is performed to the outer surface side of the welded portion by a reflection method of 1.0 skip using the transducer group on the side far from the welded portion. The flaw detection can be performed to the entire surface and the entire length of the welded portion (from the outer surface side to the inner surface side of the steel pipe) by repeating the steps 1-4 as well as mechanically scanning the relative position between the steel pipe and the linear array probe in the pipe axis direction.

Note that the diameter of the transmission beam 8 is set from the wave transmission transducer group 6 to the range from 0.5 mm to 2.5 mm with respect to the welded surface of the welded portion 2 in the pipe axis direction of the pipe body 1, and the beam 8 is transmitted. Likewise, the wave reception transducer group 7 also sets the beam width of the received beam to the range from 0.5 mm to 2.5 mm.

Sample pipes were made under various conditions likewise the experiment of the C-scan, and the flaw detection was performed to the steel pipe itself by the method shown in FIG. 11 also in the tandem flaw detection. Thereafter, Charpy test pieces were made from the portions subjected to the flaw detection, a Charpy impact test was performed to the Charpy test pieces at −40° C., and signal intensity was compared with absorbed energy. In the experiment, after the beam size of the ultrasonic wave was set to 1.4 mm×1.4 mm and the sensitivity of the echo of a 1.6 mmϕ drilled hole passing through a seam portion in the wall thickness direction was set to 80%, the flaw detection was performed by increasing the sensitivity 20 dB.

Figure 13:
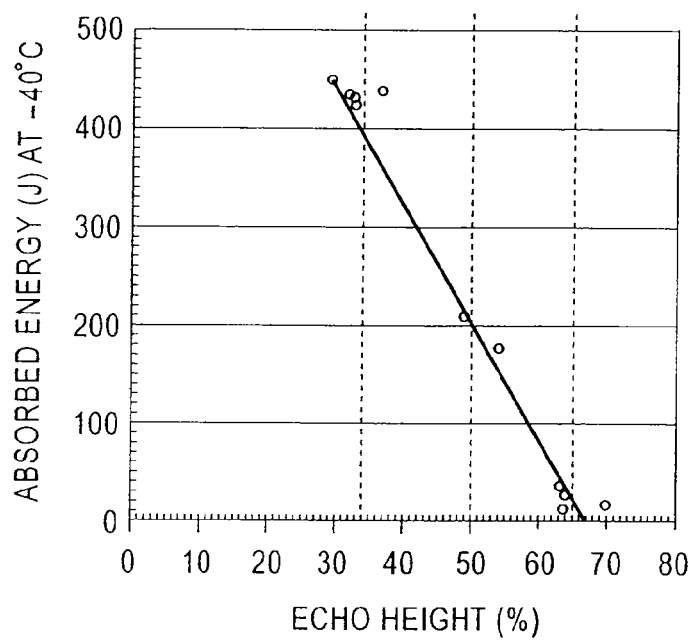
FIG. 13 is a view showing the relation between an echo height and absorbed energy likewise.
Figure 14:
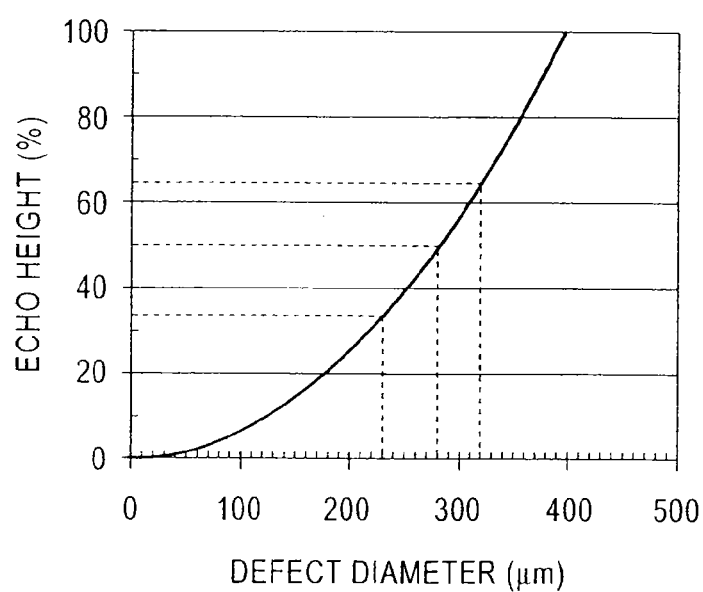
FIG. 14 is a view showing the correlation between a defect diameter and an echo height likewise.

FIG. 13 shows a result of the experiment. As can be found from the drawing, the signal intensity is correlated with the absorbed energy likewise the case of the C-scan, and when an echo height was 34% or less, the absorbed energy was 400 J, when an echo height was 50%, the absorbed energy was 200 J, and when an echo height was 65% or more, the absorbed energy was 20 J. Further, since the relation between the signal intensity (echo height) and a defect diameter when the sensitivity is set as shown in FIG. 14, the echo height of 34% corresponds to a defect diameter of 230 μm, the echo height of 50% corresponds to a defect diameter of 280 μm, and the echo height of 65% corresponds to a defect diameter of 320 μm. Note that, in FIG. 14, when an equivalent defect diameter is converted into a defect density and caused to correspond to FIG. 13, a minute penetrator density (defect density) can be caused to correspond to the absorbed energy as shown in FIG. 15.

As described above, it can be found that an equivalent defect diameter calculated from a detected result can be caused to correspond to a mechanical characteristic value when a quality control is performed by detecting a scattering type penetrator even in the tandem flaw detection which can inspect a flaw of a welded portion of a steel pipe itself. Sensitivity can be calibrated by measuring an artificial defect whose size is previously known and comparing the defect diameter of the artificial defect with the equivalent defect diameter based on the knowledge.

It is sufficient to calibrate the sensitivity by a procedure shown in, for example, FIG. 16, and the procedure will be explained together with a schematic view of sensitivity adjustment shown in FIG. 17.

Figure 15:
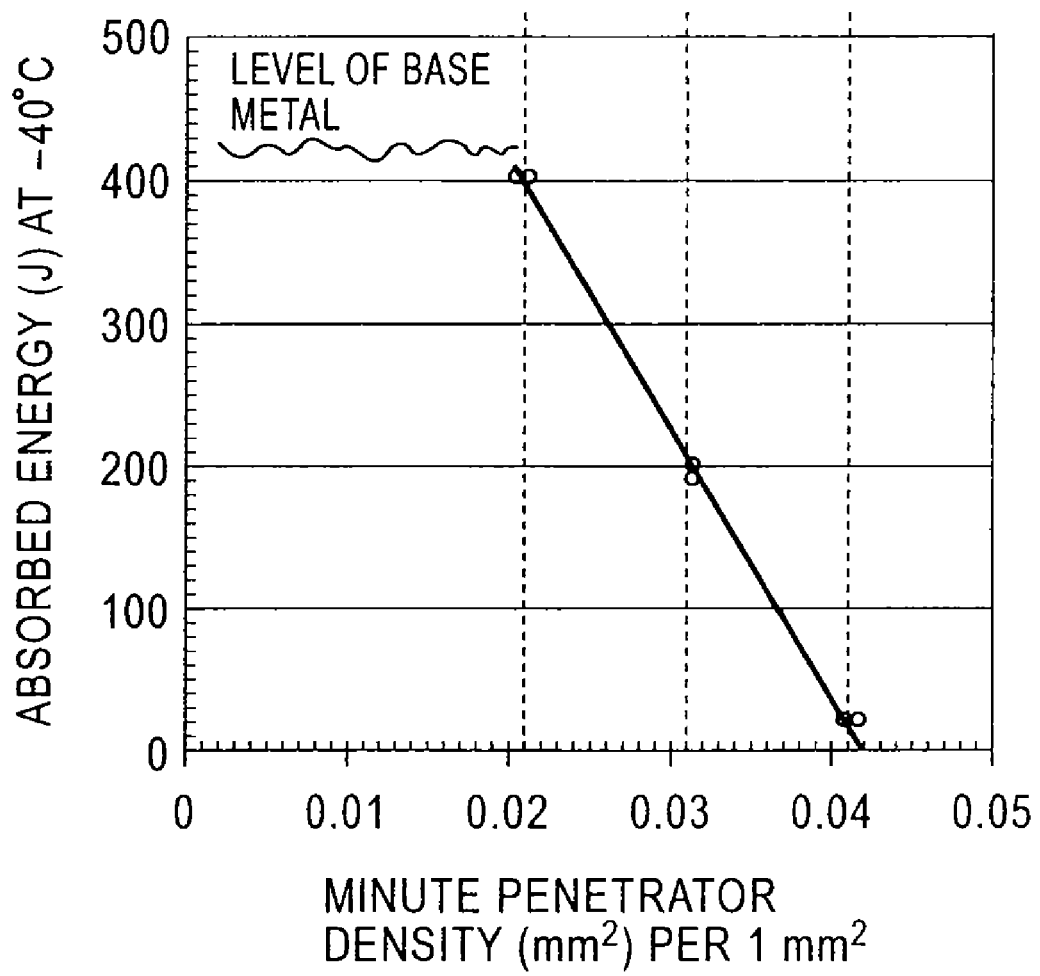
FIG. 15 is a view showing the correlation between a minute penetrator density and absorbed energy likewise.

First, a corresponding defect density is determined at step S2 using a relation as shown in FIG. 15 in accordance with the mechanical characteristic value of a required specification input at step S1.

Next, at step S3, a total in-beam area S is calculated in accordance with beam sizes a, b. Note that, in the tandem flaw detection, since a beam shape is made to a rectangular shape because the array probe is used, the beam sizes a, b show the lengths of the respective sides of a rectangle.

$$S = a \cdot b \cdot dp \qquad (1)$$

where, a, b show beam sizes in a thickness direction and in a longer direction, and dp shows a defect density.

Here, a·b show a beam area. However, in the case of the C-scan, since a beam shape is a circular shape or an oval shape, it is sufficient to determine Expression (1) so that a beam area can be obtained in accordance with the shape.

Next, at step S4, the difference of intensity to the artificial defect, which is used to calibrate the sensitivity, is calculated. Specifically the acoustic reflectivity R1 of, for example, a circular plane flaw can be shown by the following expression.

When acoustic reflectivity in a scattering type penetrator is determined, Expression (2) calculates it using an equivalent defect diameter.

$$R1 = (2\pi r^2)/(\lambda x) = (2S)/(\lambda x) \quad (2)$$

where, r shows the radius of an equivalent defect (circular defect of the total in-beam area), λ shows a wavelength, and x shows the distance from a defect.

Further, a drilled hole ordinarily used in an artificial defect may be considered as a columnar flaw, and the acoustic reflectivity R2 of the columnar flaw can be shown by the following expression.

$$R2 = \sqrt{\{r/(r+x)\}} \quad (3)$$

Accordingly, the difference ΔG of signal intensity between an equivalent defect and a drilled hole can be determined from R1, R2 by the following expression.

$$\Delta G = 20 * \log(R1/R2) \text{ (dB)} \quad (4)$$

Next, at step S5, sensitivity correction is performed so that an echo height can be accurately processed and set to a range in which it can be determined when a signal is processed, and a threshold value for determining a defect is determined. When, for example, difference ΔG of signal intensity=−30 dB is determined at step S4 and when the strength of a drilled hole DH is set to 100% on a chart (set to the maximum value of a dynamic range in a signal processing), since −30 dB is 3.1% of the maximum value of the dynamic range, it can not be recognized on the chart (in the signal processing) because it is excessively low. To cope with the above problem, when a sensitivity correction of, for example, 20 dB (10 times) and the like is performed, since the threshold value is set to 31%, it can be accurately determined on the chart as well as by the calculation of the signal processing. It is preferable to set the threshold value to the range of 20-60%, and it is sufficient to determine the sensitivity correction amount based on the difference ΔG of signal intensity so that it is within the range.

Next, the process goes to step S6 at which a steel pipe for calibration having an artificial defect (for example, a 1.6 mmφ drilled hole) is measured, and the sensitivity (gain) of a received signal amplifier, which amplifies a signal received thereby so that it is set to a predetermined level, is adjusted. Note that the predetermined level is preferably set to a value corresponding to 100% on a chart or to the maximum value of a dynamic range in a signal processing device. This corresponds to gain setting 1 of FIG. 17.

Next, the process goes to step S7 at which the sensitivity adjustment (gain adjustment) is further performed to the received signal amplifier in correspondence with the sensitivity correction amount set at step S5. This corresponds to gain setting 2 of FIG. 17.

Next, at step S8, a flaw detection is performed using the threshold value determined at step S5.

As described above, the sensitivity is adjusted so that, for example, the echo height of the artificial defect is used as the reference value, and a threshold value for evaluating the mechanical characteristics of a welded portion can be determined by the echo height to the reference value.

The calibration method according to embodiments of the present invention is as explained above. However, since various examinations are performed to apply the tandem flaw detection method described above to a welded portion of a electric resistance welded steel pipe, they will be specifically explained below in detail.

First, as to the determination of an aperture width of the array probe 1, it is sufficient to consider as described below.

FIG. 18(a) is a view showing the relation between a beam width (beam size corresponding to one side of a square, shown as beam size in FIG. 18) and the equivalent defect diameter (total in-beam defect area). As to a case in which defect densities are set to 0.03 mm² and 0.02 mm², the equivalent defect diameter is theoretically calculated when the total area of the defects existing in an ultrasonic beam is shown by the equivalent defect diameter and the beam width (beam size) is changed. Although an increase of a beam width increases the equivalent defect diameter, it is saturated and set to a predetermined value when the beam width increases to 1.5 mm or more. A reason why the equivalent defect diameter is saturated as described above resides in that it is assumed that the distribution range of scattering penetrators is 1.5 mm×1.5 mm.

FIG. 18(b) is a view of signal intensity at the time when it is calculated from the acoustic reflectivity corresponding to the equivalent defect diameter shown in FIG. 18(a) described above and shown by dB in the tandem flaw detection. A noise level of −40 dB is drawn as a level which will be approximately obtained actually in the tandem flaw detection. A reason why the noise level is increased on the side where the beam width (beam size) is large resides in that when the beam size is increased, noise caused by the surface roughness on inner and outer surface is detected. It can be found that the range of the beam width of 0.5-2.5 mm, in which a noise level is smaller than a signal level, is a range which can be applied to the tandem flaw detection. Further, when the defect density is 0.02 mm², since the signal intensity is somewhat lowered, the applicable range is from a beam width exceeding 0.7 mm to 2.5 mm. Furthermore, to obtain a good S/N ratio, the range of 1-2 mm is more preferable because it is desirable that the difference between the signal level and the noise level is 5 dB or more.

In contrast, FIG. 18(c) is view in which the signal intensity of the equivalent defect diameter is calculated and shown by dB to compare the difference between the tandem flaw detection and the C-scan. FIG. 18(c) shows the signal level as to a case that the defect density is only 0.03 mm². In the C-scan, since the signal intensity exceeds the noise level in the range of the beam width of 0.2-1 mm, this range is an application range for detecting scattering penetrations. A reason why the beam width is set to 440 μm in the embodiment using the C-scan in FIG. 7 described above resides in that the difference between the signal intensity and the noise level is largest at the time and S/N is made good in the range. Note that a reason why the application range is different between the C-scan and the tandem flaw detection resides in that the noise level in the C-scan is lower than that of the tandem method because conditions are good in that a water distance is short, a surface is a polished surface, and the like. In contrast, this is because when a beam size exceeds 1 mm, S/N is deteriorated by the influence of the side surface of a sample (since a beam transmission path is shut off and diffused reflection occurs on the side surface of the sample, the noise signal thereof is collected).

Accordingly, when the tandem method is used, the aperture width is set so that a beam width (beam size) different from that of the C-scan can be obtained.

Figure 19:
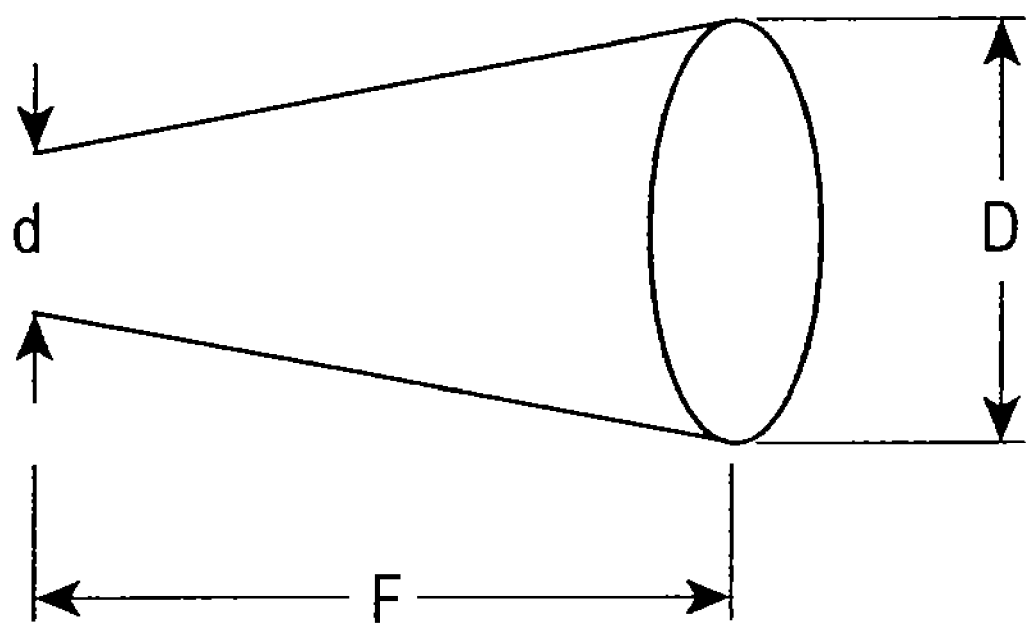
FIG. 19 is a view showing the relation between an aperture width and a beam size.

Note that the aperture width D of a transducer for obtaining a beam width d in the tandem flaw detection can be determined by the following expression.

$$D = \lambda \cdot \frac{F}{d \cdot \sin\theta} \cdot \frac{\cos\theta w}{\cos\theta} \quad (5)$$

where, d shows a beam size at a flaw detection position as shown in FIG. 19, F shows focal length, λ shows a wavelength, θ shows a refraction angle, and θw shows an incident angle.

When, for example, a water distance is set to 30 mm, a path in steel is set to 24 mm, a refraction angle θ=45°, an incident angle θw=18.9°, a focal length F is 30+24/1480×3230=82 mm, and when a frequency is set to 10 MHz, a wavelength λ is 1480/10 MHz=0.148 mm. Accordingly, the aperture width D for obtaining beam width d=1.5 mm can be determined from Expression (5) as D=15.

The number of the transducers of a transducer group is determined by the aperture width determined as described above. Although the number of the transducers of the transducer group may be set to a predetermined number, the number of the transducers of each scan line may be changed to obtain uniform sensitivity. More specifically, in the tandem flaw detection using the array probe, transducer groups nearer to a welded portion side of the transducer groups have a shorter focal length and transducer groups farther from the welded portion side have a longer focal length. Accordingly, the aperture width is determined as well as the number of transducers which are excited at the same time are determined in consideration of the focal length F in accordance with the position of a transducer so that the beam width is within the above range or the beam width is set to a predetermined width. Then, a control is performed so that the number of transducers corresponding to the aperture width is excited at the same time. Note that the number of the transducers which are excited at the same time means the number of transducers of a transducer group used to transmit and receive a wave once. Then, a delay time is set to respective elements in the transducer group to control focusing and deflection.

Figure 21:
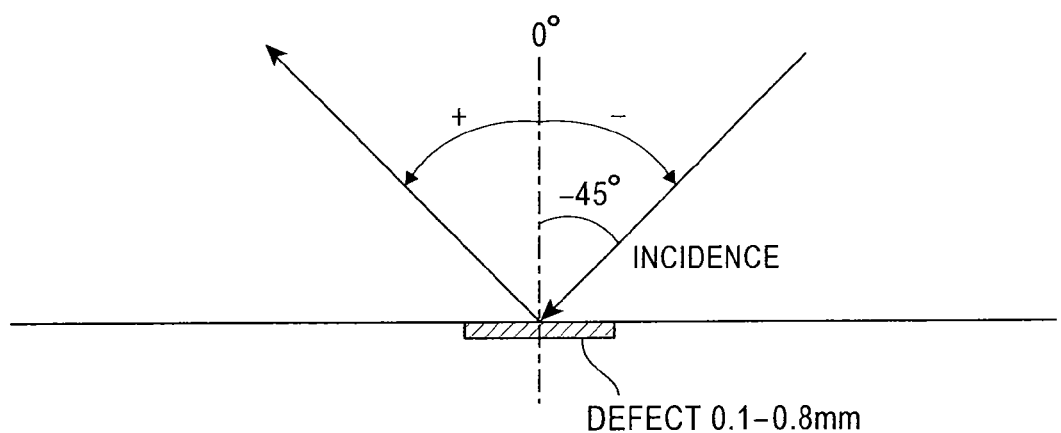
FIG. 21 is a view explaining reflection characteristics.

Next, it is sufficient to determine an incident angle and a reflection angle to a welded surface as shown below. FIG. 20 shows a result of theoretical examination of the relation between the size of a defect and reflection directivity. As shown in FIG. 21, a result shown in FIG. 20 is obtained by causing an ultrasonic wave to be incident from a −45° direction and theoretically calculating the signal intensity at respective reflection angles under the condition of defect sizes (equivalent defect sizes) of 0.1 mm, 0.2 mm, 0.4 mm, and 0.8 mm corresponding to a pipe wall thickness direction (corresponding to a lateral direction in FIG. 21), respectively at frequencies of 10 MHz, 15 MHz, and 20 MHz. Note that a vertical axis of FIG. 20 is shown by a relative value which is standardized by setting the signal intensity at 45° that is a normal reflection angle to a reference value 1. In any case, the signal intensity of a reflected wave reflecting in the −45° direction at which the ultrasonic wave is incident is very low and about 0.2 or less of a normal reflection direction 45°. It can be found that the 45° direction that is the normal reflection direction is strongest in any case.

At 20 MHz of a defect size of 0.8 mm in which the directivity is acutest, the angle at which the signal intensity is set to half that of the normal reflection angle (value in FIG. 20 is set to 0.5) is within the range of 40°-50°. As described above, since the directivity is different depending on a defect size, it is sufficient to determine an incident angle of a received beam depending on the size of a defect desired to be detected. To detect, for example, a larger defect without lowering the sensitivity, it is preferable that the incident angle of the received beam to a welded portion be an angle near to 45°, and the incident angle is preferably within the range of from 39° to 52° to suppress the reduction of the signal intensity of a defect of 0.8 mm to half of it at, for example, 15 MHz. On the contrary, the incident angle is preferably within the range of from 33° to 61° when a defect of only 0.4 mm or less is a target at, for example, 15 MHz.

Since it is found by the analysis that the signal intensity of the reflected signal of an ultrasonic wave in a defect is increased with a peak in the normal reflection direction, it is most preferable to receive the ultrasonic wave in the normal reflection direction. However, since a defect can be sufficiently detected when reflection strength is 50% of the peak, it is sufficient to receive an ultrasonic wave which is reflected in an angle range corresponding to the range.

Judging from the result of the reflection directivity of the defect size 0.4 mm at the frequency of 15 MHz shown in FIG. 20, since the reflection angle at which reflection intensity is set to 50% or more of the peak is 33°-61°, the preferable range of the incident angle is the range of −12°-+16° using 45° that is the normal reflection angle as a reference. Further, the target is expanded up to a defect size of 0.8 mm at a frequency of 20 MHz, the preferable range is the range of from −5° to +5° to the normal reflection angle. Although reflection angle characteristics are shown by the incident angle of 45° to a defect in the example described above, the same result can be also obtained as to the incident angle characteristics when an opposite reflection angle is set to 45°. Further, an incident angle other than 45° may be employed, and approximately the same characteristics can be obtained when the incident angle is within the range in which the condition of a mode conversion loss can be cleared.

Note that a refraction angle suitable for a flaw detection in a shear wave can be applied in the range of about from 30° to 70° when the mode conversion loss is taken into consideration. However, when the angle dependency of acoustic reflectivity at the time a shear wave is reflected at a defect and on an inner surface is taken into consideration, the range of about from 35° to 55° at which the shear wave is totally reflected is preferable. Further, the incident angle may be set to the range of 40°-50° in consideration of safety. Further, although it is most preferable that a transmitted wave and a received wave have the same refraction angle, the refraction angle of the transmitted wave may be different from that of the received wave within the range of the reflection directivity of a defect because the reflection directivity is broad.

Figure 22:
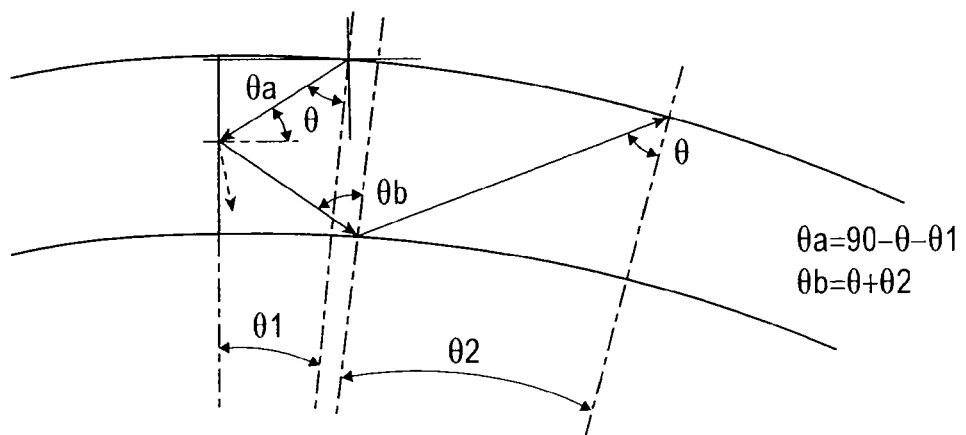
FIG. 22 is a view explaining a mode conversion loss in a steel pipe.

A procedure for setting the refraction angle to the range in which no mode conversion loss is generated will be explained referring to FIG. 22.

1) A refraction angle is determined as well as the position and the angle of an array probe is determined.

1)-1: The incident angle θ is determined in consideration of an incident angle θa to a welded surface. A theoretical incident angle to the welded surface at which no mode conversion loss is generated is 33.2°≦θa≦56.8°. When the incident angle is within the above range, it may not be fixed but may be changed when the welded surface is scanned from an inner surface to an outer surface in a pipe wall thickness direction. Accordingly, an example, in which the refraction angle θ is fixed to make a calculation easy, will be shown. Here, the incident angle θa to the welded surface is shown by θa=90°−θ−θ1, and θ1 is changed in the range of from 0 to θ2 depending on the position of a welded portion in the wall thickness direction (for example, θ1=θ2 on the inner surface side, and θ1=0 on the outer surface side). When, for example, θ2=4° and the refraction angle is 45°, θa=from 41° to 45°. Further, when an ultrasonic wave has the refraction angle of 47° at the time it is incident in the vicinity of the center of the pipe wall thickness of the welded portion, θa=about 45° at the center of the welded portion in the wall thickness direction, and the scan is performed on the inner and outer surfaces within the range of θa=from 43° to 47°.

1)-2: The position and the angle of the array probe are determined so that an ultrasonic beam, which is transmitted from a transducer positioned at the center of the array probe in a direction vertical to the surface of the array probe, is incident from the outer surface side of a steel pipe as a shear wave at a predetermined refraction angle (for example, 45°) and incident on the position at the edge on the inner surface side (or at the edge on the outer surface side) of a welded surface at a predetermined incident angle (for example, 41° in the example described above).

2) The position, at which a scan line transmitted and received from and to each transducer of the array probe is incident on the outer surface of the pipe, is determined.

2)-1: Although the position is determined by various methods, for example, as to a transducer as a target (or a position between transducers), a scan is performed on the outer surface of the pipe, the refraction angle θ, which is determined by the position of the transducer, an outer surface scan position, and an outer surface tangential line, is calculated, and an incident position on the outer surface at which θ is set to the value determined in 1)-1 is determined. Specifically, scan lines are determined by connecting respective transducers to respective points on the outer surface (for example, the respective points are disposed on an outer periphery at equal intervals and at arbitrary intervals) by straight lines, a refraction angle θ is calculated as to each of the scan lines, a scan line whose θ is the same as or nearest to a predetermined refraction angle is selected, and the incident position of the scan line is determined as the above position.

2)-2: A transmission path after the beam is incident on the pipe is geometrically determined from the position of the transducer, the incident position on the outer surface determined in 2)-1, and a pipe shape (diameter and thickness), and an incident position to the welded surface is determined.

3) Since the positioning is performed in 1) at the center of the array probe and the above processing is performed at the predetermined refraction angle, a combination (pair) of the transmission paths (scan lines) determined in 2)-2 is made symmetrically on the welded surface using the scan line at the center of the array probe as a reference. The scan lines of the pair are used as scan lines for transmitting and receiving the beam and arranged as central transducers of a wave transmission unit and a wave reception unit (the transducer groups of the wave transmission unit and the wave reception unit are formed about the transducers). Note that when the number of the transducer groups is an even number, the processing is performed after a center position is corrected to the boundary of the transducers. Further, although a calculation is performed assuming that the refraction angle θ is fixed, the calculation may be performed assuming the incident angle θa to the welded surface is fixed, or it is also possible to change both θ and θa.

A control procedure of the transducer group for scanning a beam in the thickness direction of a welded surface will be explained using an ultrasonic flaw detection apparatus. Specifically, it is sufficient to determine wave transmission and reception transducer groups, the number of transducers, a deflection angle, and a focal length by the following procedure. The width of the transducer groups used in a wave transmission unit and a wave reception unit is determined from a focusing coefficient from which necessary sensitivity can be obtained so that a refraction angle is set to a predetermined angle, and this will be explained appropriately referring to FIG. 11 or 23. Note that since the contents of a), b), g) shown below correspond to 1), 2), 3) described above, they will be briefly explained here.

a) The position of a linear array probe is determined so that an ultrasonic beam, which is transmitted from a transducer positioned at the center of the linear array probe in a direction vertical to the surface of the array probe, is incident on a steel pipe as a shear wave at a predetermined refraction angle (for example, 45°) and incident on the inner surface side or the outer surface side of the steel pipe of a welded portion.

b) Incident points are geometrically determined so that the incident angles from respective transducers to the outer surface of the steel pipe are fixed at all times or within a predetermined range, and further lines (scan lines) passing in the steel pipe at a refraction angle 45° are determined.

The respective transducers referred to here are transducers corresponding to the center position of the wave transmission unit, and the positional relation between the transducer groups of the wave transmission unit and the incident points on the outer surface of the steel pipe is determined. Further, a transmission path after an ultrasonic beam is incident on the steel pipe, i.e, a reflection point on the inner surface, a reflection point on the outer surface, and a reflection point on a welded surface are determined in correspondence to a refraction angle.

c) A deflection angle of each scan line is calculated from the positional relation between the incident points and each transducer.

d) A water distance of each scan line and a path in steel up to a welded portion are calculated, and a focal length in water F is determined by converting them by a sound speed and a water distance.

e) The number n of the transducers of the transducer group of each scan line (corresponding to "the number of transducers excited at the same time") is determined by calculating an aperture width D of the each scan line in conformity with a necessary beam width d using Expression (5), dividing the aperture width D by a transducer pitch and rounding off a resultant quotient. Note that the necessary beam width d means the range of a beam diameter applied to detect a scattering type penetrator showing a mode in which minute defects are distributed in a wide range as described above, and the range is from 0.5 to 2.5 mm, preferably more than 0.7 mm to 2.5 mm, and more preferably 1.0-2.0 mm.

f) The position of each transducer group constituting the wave transmission unit is determined from the position of the transducer of each scan line and the number of transducers n.

g) A scan line used to a flaw detection is determined from the positional relation intersecting at the welded portion of each scan line as well as a wave reception transducer group, which is arranged as a pair with a wave transmission transducer group, is determined. It is sufficient to select a pair of scan lines, which are transmitted from an opposite direction and intersect at the welded portion, as a pair of a wave transmission unit and a wave reception unit. Further, when scan lines are unnecessarily overlapped to spatial resolution required to the same position of the welded portion, they may be thinned out.

h) Since the number of transducer groups, the focal length, and the deflection angle are determined as to all the scan lines used for the flaw detection, delay times applied to the respective transducers are calculated, respectively. As to a method of calculating the delay times, it is sufficient to utilize the known technology disclosed in Patent Document 5 applied by the inventors.

Figure 24:
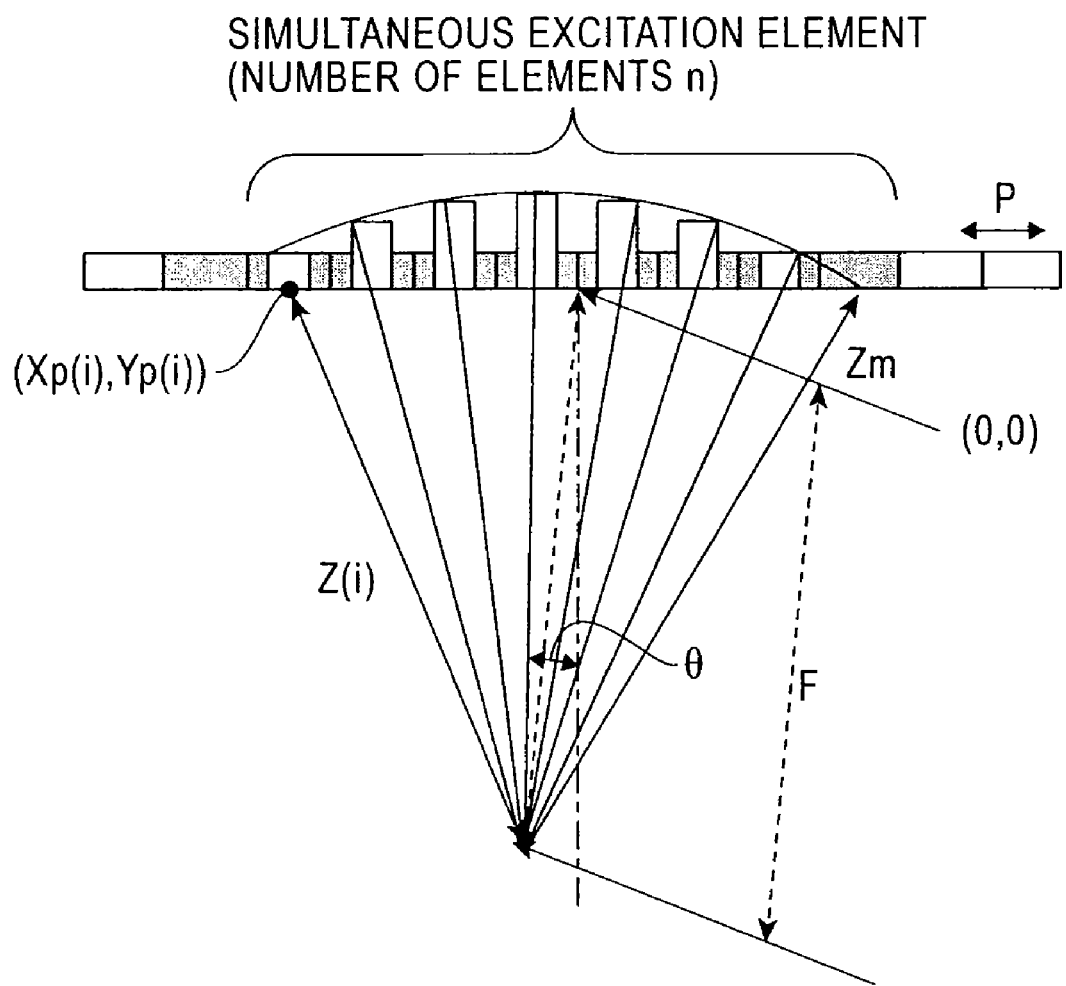
FIG. 24 is a view explaining a calculation of a delay time applied to respective transducers.

A basic way of thinking of the calculation will be explained below referring to FIG. 24 and an expression. First, the center position of a transducer group is set as an origin of a coordinate, a focal length is shown by F, and a deflection angle is shown by θ, and a coordinate of a focus position {Xf, Yf} is determined as shown below.

$$Xf = F \cdot \sin\theta, \; yf = -f \cdot \cos\theta$$

Next, a transducer pitch is shown by P, the number of transducers of a transducer group is shown by n (n is an even number), and a coordinate {Xp(i), Yp(i)} of each transducer is determined.

$$Xp(i) = -n \cdot p/2 - p/2 + p \cdot i, \; Yp(i) = O \; (i=\text{from 1 to } n)$$

Further, a distance Z(i) between the focus position and each transducer and the maximum value Zm of the distance are determined.

$$Z(i) = \text{SQRT}\{(Xf - Xp(i))^2 + (Yf - Yp(i))^2\} \; (i=\text{from 1 to } n)$$

$$Zm = \max\{Z(i)\} \; (i=\text{from 1 to } n)$$

Finally, a delay time Δt(i) is determined by the following expression. Note that C shows a sound speed.

$$\Delta t(i) = (Zm - Z(i))/C \; (i=\text{from 1 to } n)$$

Note that, although the basic way of thinking of the calculation is shown above, it is not always necessary to set the center position of the transducer group as the origin of the coordinate as to each of the respective scan lines. Further, although the number of the transducers n is the even number in the above explanation, it may be an odd number. When it is set to the odd number, it is needless to say that the above expressions can be applied thereto by being modified partly. In an actual calculation, it is sufficient to previously determine a coordinate of each element of an array prove, to determine a coordinate of a focus position in accordance with a focal length and a deflection angle, and to determine a distance Z(i) between the focus position and each transducer.

Figure 23:
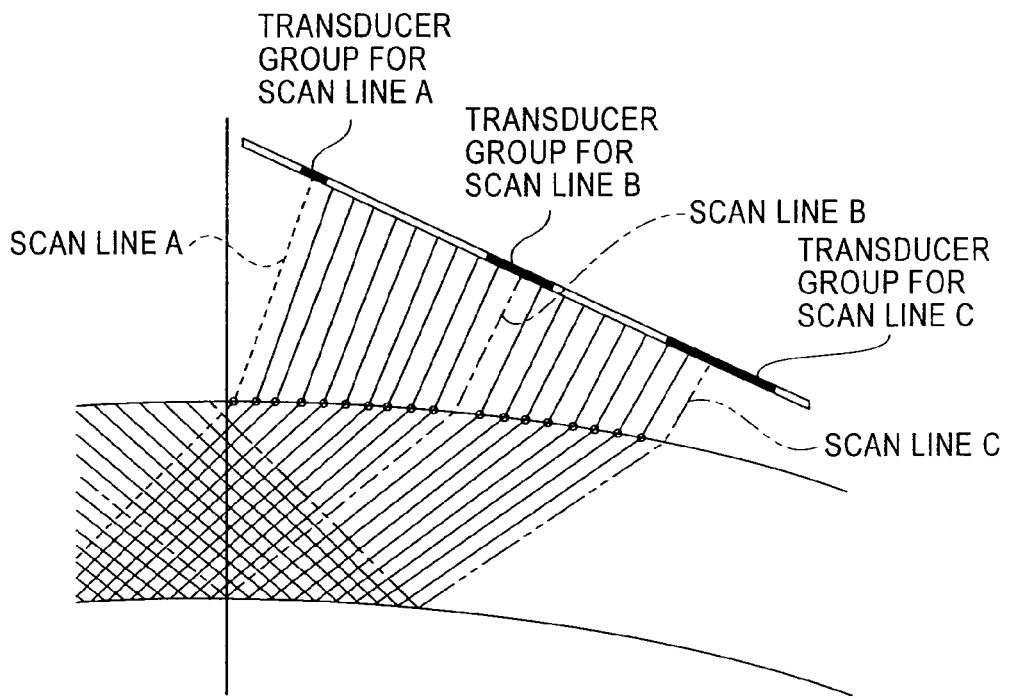
FIG. 23 is a view showing a scan line and an example of a result of calculation of a flaw detection condition of representative points.

FIG. 23 is a view showing an example of scan lines determined as described above and a result of calculation of a flaw detection condition of representative points of the scan lines. FIG. 23 shows an example of inspecting a flaw of a steel pipe having an outside diameter of 558.8 mmφ and a wall thickness of 25.4 mm by a linear array probe having 160 elements (transducers) under the conditions of an ultrasonic frequency of 15 MHz, a distance between transducers set to 0.5 mm pitch, a center water distance of 20 mm, and a refraction angle of 45°. The transducers have a number 1 on a side near to a welded portion and a number 160 on a side far from the welded portion.

Figure 25:
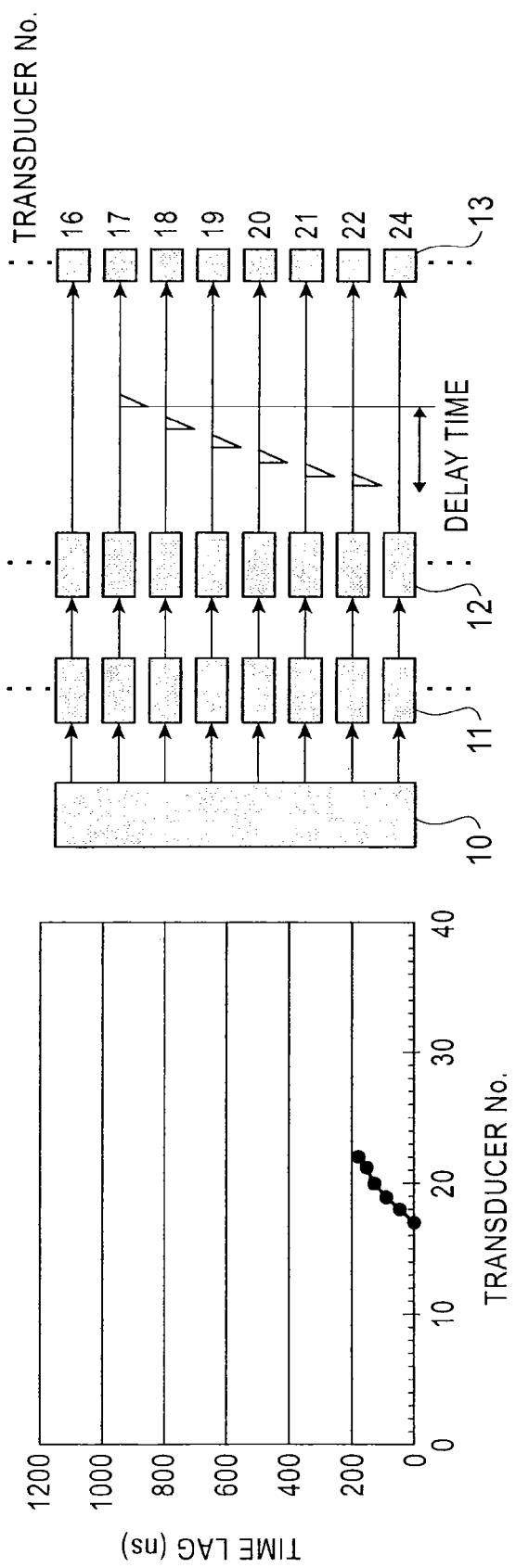
FIG. 25 is a view showing a result of calculation of a delay time calculated as to a scan line A and a principle of wave transmission.

FIG. 25 is a view showing a result of calculation of a delay time calculated as to a scan line A shown in FIG. 23 and a principle of wave transmission. In FIG. 25, 10 denotes a flaw inspecting condition calculation unit for performing calculations from 1) to 8) described above, 11 denotes a delay time setting unit for determining timing at which wave transmission pulses are transmitted based on the calculations, 12 denotes a pulser, and 13 denotes respective transducers of the linear array probe 5. FIG. 25 shows that only the transducers Nos. 17-22 are selected, the transducer No. 17 is excited first, and the transducers Nos. 18-22 are gradually excited with a delay time. With this operation, a transmission beam corresponding to the scan line A is formed.

Figure 26:
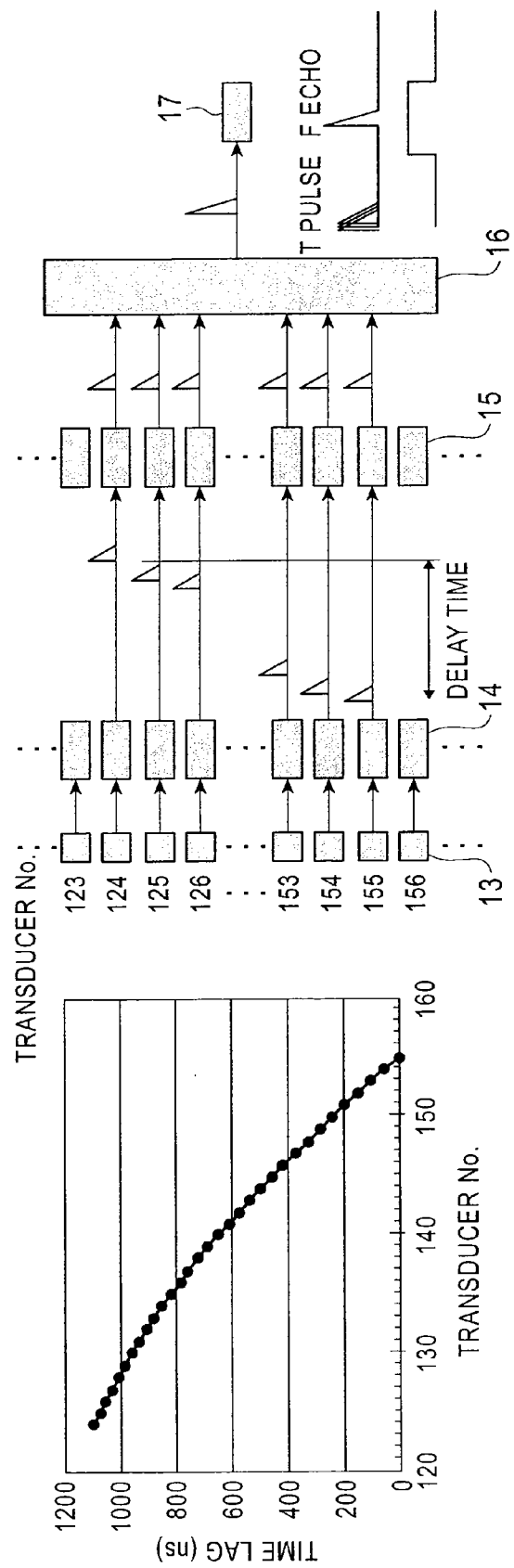
FIG. 26 is a view showing a result of calculation of a delay time calculated as to a scan line C and a principle of wave reception.

FIG. 26 is a view showing a result of calculation of a delay time calculated as to a scan line C shown in FIG. 23 and a principle of wave reception. In FIG. 26, 13 denotes respective transducers of the linear array probe, 14 denotes a receiving amplifier, 15 denotes a delay time setting unit, 16 denotes a synthesization processing unit, and 17 denotes a gate evaluation unit. FIG. 26 shows that only the transducers Nos. 124-155 are selected, an echo from a defect is incident on the transducer No. 124 first and gradually received by the transducers No. 125-155 with a delay time, the delay time is corrected by the delay time setting unit 15 so that phases are caused to agree with each other, the echoes are synthesized by the synthesization processing unit 16, and the size of the synthesized echo is increased by a focusing effect.

With this operation, a wave corresponding to the scan line C is received. Thereafter, the gate evaluation unit 17 determines whether or not a defective echo (F echo in the drawing) exists from a transmitted pulse (T pulse in the drawing) in a time region (gate) set to a distance corresponding to a beam path, and a flaw detection is performed. Note that the delay time setting unit 15, the synthesization processing unit 16, and the gate evaluation unit 17 may also subject a signal to A/D conversion just after it is output from the receiving amplifier 14, stores the signal to a memory, and then process the signal by software.

In the above explanation, although the flaw detection condition is sequentially calculated after the incident points of the respective scan lines are determined first, the calculation is not restricted thereto. For example, the calculation may be performed by determining a focus position and thereafter searching and determining a path in which a transmission time up to the focus position is shortest as to respective transducers.

Note that, to evaluate the mechanical characteristics of a welded portion of a electric resistance welded steel pipe in the tandem flaw detection, although the beam width of an ultrasonic wave to be transmitted and received must be set to 0.5-2.5 mm, a focusing coefficient, which is one of parameters for showing the degree of focusing of the beam also has a range to which it can be applied. The focusing coefficient J is a value showing an increase of sound pressure at a focusing position.

$$J = 20\log\left(\frac{D^2}{4\lambda F}\right) \tag{6}$$

where, D shows an aperture width of a transducer, F shows a focal length, and λ shows a wavelength. Note that in Expression (6), values converted in water are used as the focal length F and the wave length λ.

Figure 27:
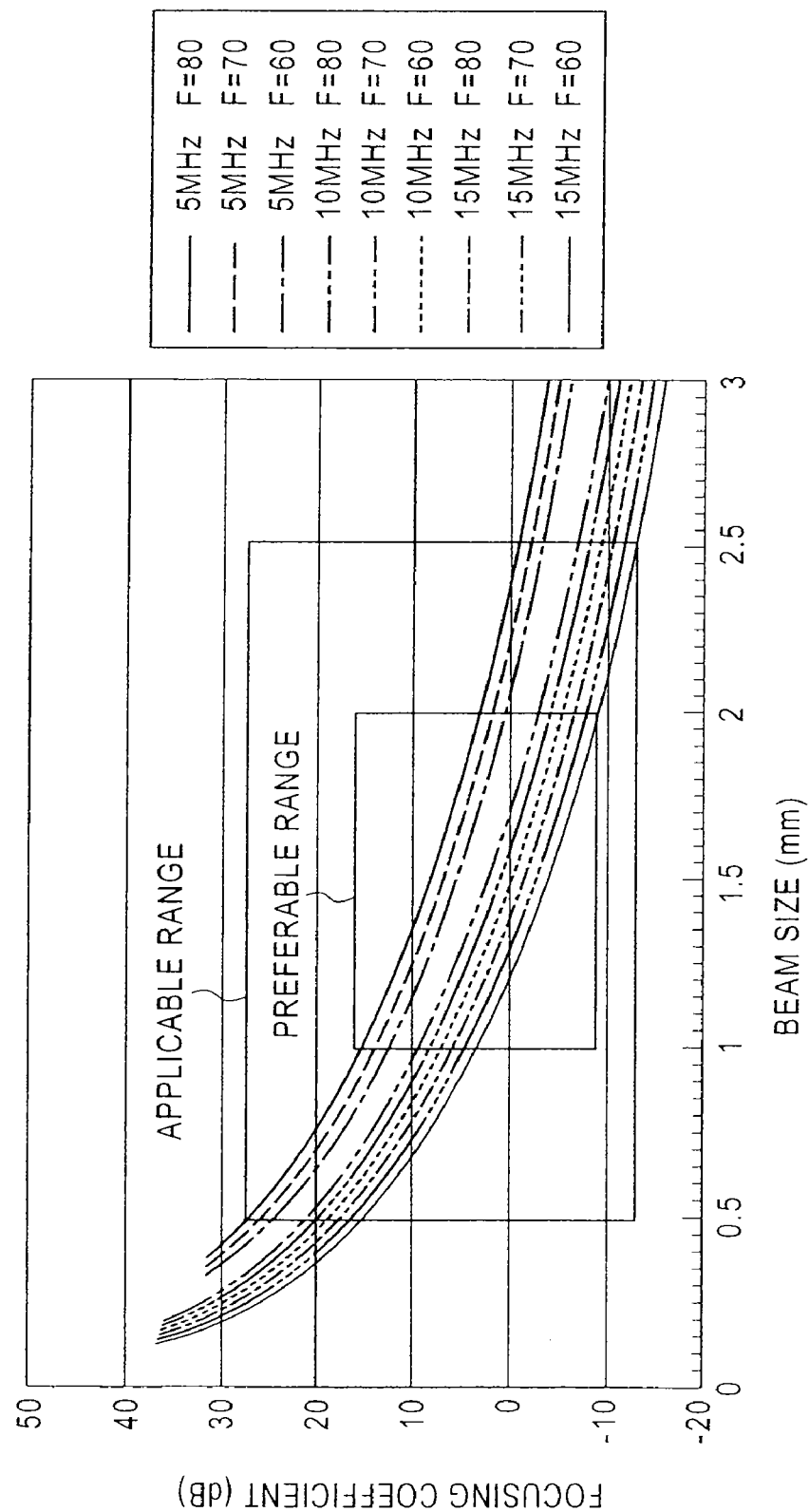
FIG. 27 is a view showing the relation between a focusing coefficient and a beam size.

FIG. 27 shows a result of a theoretical calculation of the relation between a focusing coefficient and a beam width (beam size, shown as a beam size in FIG. 27) using Expression (6) under the conditions of a frequency of from 5 MHz to 15 MHz, a focal length F=from 60 mm to 80 mm (approximately corresponding to the range of the wall thickness from 10 mm to 16 mm of a steel pipe). As can be found from the relation, a smaller beam width (beam size) increases the focusing coefficient, and a larger beam width decreases the focusing coefficient. Since the focusing coefficient is a value showing an increase of the sound pressure, a larger value is better. However, in the detection of a scattering type penetrator of the mode in which minute defects are distributed in a wide range, when the focusing coefficient is increased as described above, since the beam size is made smaller than an optimum range, it is necessary or preferred to take it into consideration that the beam width is within the optimum range. When, for example, the beam width of an ultrasonic wave, which can be applied to detect a scattering type penetrator, is about from 0.5 to 2.5 mm, the focusing coefficient of from −13 dB to 28 dB is within the range in which it corresponds to the beam width itself. However, when the balance between the beam width and the focusing coefficient is taken into consideration, the application range of the focusing coefficient is about from −5 to 20 dB, and the range of about from −10 to less than 5 dB of the focusing coefficient can be applied to the preferable range of about from 1.0 to 2.0 mm of the beam width.

Example 1

Examples of the present invention will be explained below referring to drawings.

Figure 28:
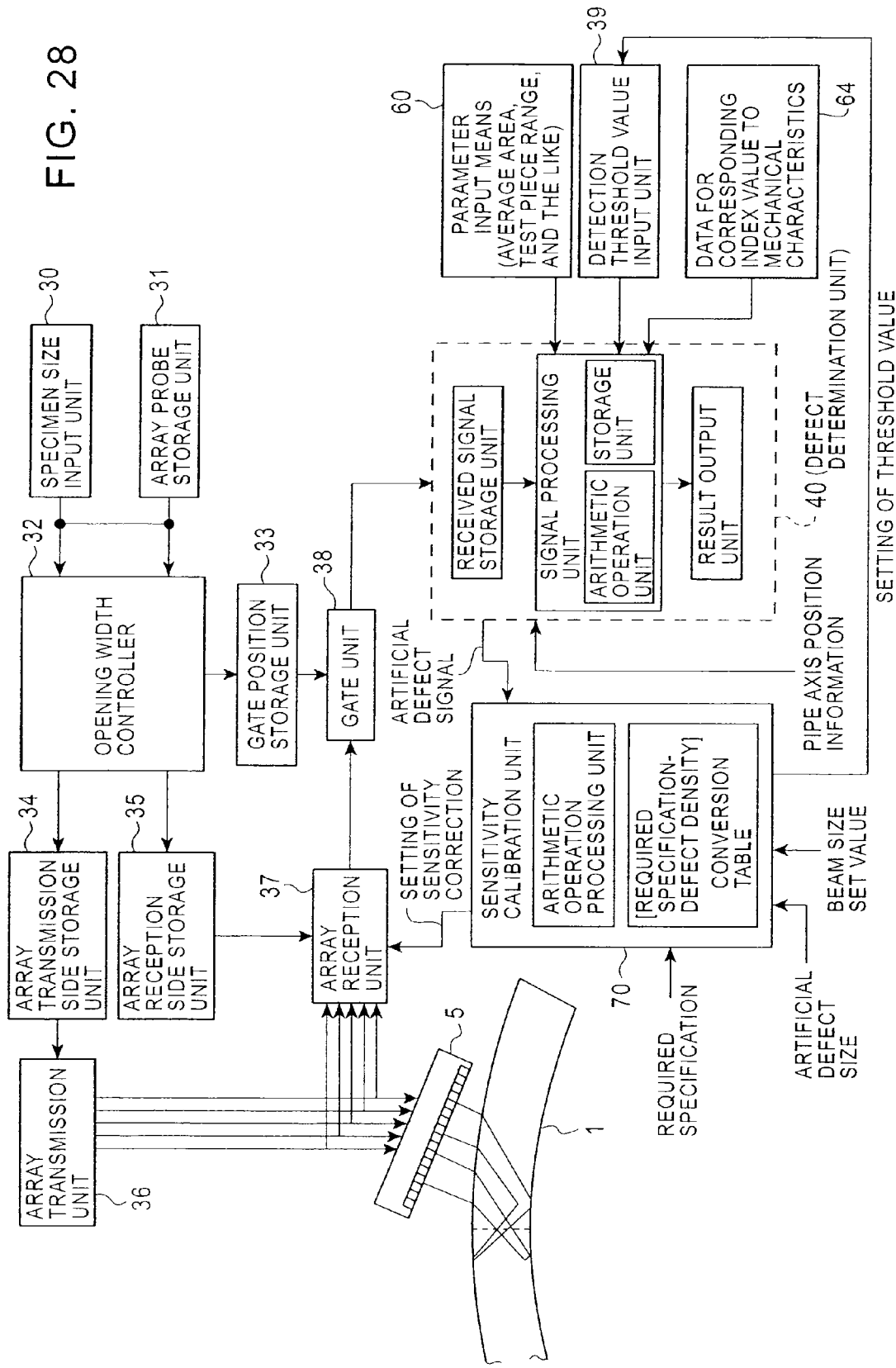
FIG. 28 is a view showing an example 1 of an ultrasonic flaw detection apparatus to which a tandem method is applied.

FIG. 28 is a view showing an example of a function arrangement of an ultrasonic flaw detection apparatus according to a tandem flaw detection. In a specimen size input unit 30, an operator or a process computer inputs the sizes of the outside diameter and the wall thickness of a steel pipe to which a flaw detection is performed. An array probe storage unit 31 stores the frequency, the transducer pitch, and the number of transducers of an array probe 5.

An aperture width controller 32 controls an aperture width corresponding to a beam width (beam size) when an ultrasonic beam is transmitted and received as well as calculates the position of a transmitting/receiving array probe, the number of wave transmission scan lines, and the path of the transmission beam of each scan line in accordance with the size of the steel pipe and the specification of the array probe. Next, a focal length and a deflection angle are determined in each of the paths. The focal length and an ultrasonic wave frequency are substituted for Expression (5), and the aperture width is determined so that the beam width is set to a predetermined range. Note that from 0.5 to 2.5 mm are applied to the predetermined range of the beam width, more than 0.7 mm to 2.5 mm are preferably applied thereto, and from 1.0 to 2.0 mm are more preferably applied thereto as described above.

The number of transducers of the wave transmission transducer group of each scan line is determined by dividing the aperture width by the transducer pitch. Then, the position of the wave transmission transducer group is determined from the position of the scan line and the number of the transducers and further the delay time of each transducer of each scan line is calculated. The respective values determined as described above are referred to as an array transmission law here.

An aperture width controller 32 calculates the position of the array probe, the number of wave reception scan lines, and the path of the reception beam of each scan line in accordance with the size of the steel pipe and the specification of the array probe. Next, the focal length and the deflection angle in each path are determined. The focal length and the ultrasonic wave frequency are substituted for Expression (5), and the aperture width is determined so that the beam width is set to the predetermined range. Note that from 0.5 to 2.5 mm are applied to the predetermined range of the beam width, more than 0.7 mm to 2.5 mm are preferably applied thereto, and from 1.0 to 2.0 mm are more preferably applied thereto as described above also when the ultrasonic wave is received likewise when it is transmitted.

The number of transducers of the wave reception transducer group of each scan line is determined by dividing the aperture width by the transducer pitch. Then, the position of the wave reception transducer group is determined from the position of the scan line and the number of the transducers and further the delay time of each transducer of each scan line is calculated. The respective values determined as described above are referred as an array reception law here. Further, a gate position for detecting a defect is determined based on the path of the beam calculated by the aperture width controller 32 and stored to a gate position storage unit 33.

Note that the array reception law may be determined based on the array transmission law, or the array reception law may be determined first and the array transmission law may be determined based on it on the contrary. The array transmission law and the array reception law which are determined as described above are stored to an array transmission law storage unit 34 and an array reception law storage unit 35, respectively, and used for the following transmission and reception control.

An array transmission unit 36 selects a wave transmission transducer group based on the array transmission law stored to the array transmission law storage unit 34 and generates transmission pulses with delay times attached to respective elements. An array reception unit 37 selects a wave reception transducer group based on the array reception law stored to the array reception law storage unit 35, adds signals with delay times attached to respective elements, and obtains a flaw detection waveform. A gate unit 38 extracts the signal of a gate position stored to the gate position storage unit 33.

When a flaw detection of one scan line is finished as described above, a next wave transmission transducer group is selected based on the array transmission law stored to the array transmission law storage unit 34, and a flaw detection is repeated likewise that mentioned above.

Note that, as to a pipe axis direction, it is sufficient to set a condition for relatively moving the array probe and a welded steel pipe. When, for example, this system is assembled to a manufacturing process, since the welded steel pipe is moved in the pipe axis direction, a scan can be performed in the pipe wall thickness direction by the array probe when it is fixed, whereas when the welded steel pipe is in a stationary state, it is sufficient to move the array prove by a mechanical structure.

A defect determination unit 40 compares an optical defect detection threshold value (threshold value) input to a detection threshold value input unit 39 with signal intensity in a gate, and when the signal intensity is equal or larger than the threshold value, the defect determination unit 40 determines a defect. The signal intensity to be compared need not be a signal itself existing in the gate and may be a calculated value (index value) after it is subjected to an average processing and a maximum value processing as shown in, for example, FIG. 8. When a flaw detection of one scan line is finished as described above, a next wave transmission transducer group is selected based on the array transmission law stored to the array transmission law storage unit 34, and a flaw detection is repeated likewise that mentioned above. Note that a defect may be determined when the signal intensity is equal or larger than the threshold value a plurality of times.

A sensitivity calibration unit performs a sensitivity calibration of the present invention. A procedure of the sensitivity calibration will be explained together with FIG. 16 explained in the example.

First, the sensitivity calibration unit 70 can input a manufacturing condition and a product specification between it and a process computer and inputs required specifications (the mechanical property of a welded portion, for example, the allowable value of absorbed energy in a Charpy impact test) relating to the mechanical characteristics of a electric resistance welded steel pipe to be manufactured and inspected from the process computer before a data inspection is started (step S1).

A defect density is determined in accordance with the mechanical characteristic values of the input required specifications using a relation as shown in FIG. 15. Note that it is sufficient to previously determine the data shown in FIG. 15 in comparison with a lot of samples and to store the data as an expression for calculating the defect density from the mechanical characteristics or as table data (step S2).

A beam size to be set is input from the aperture width controller 32, and a total in-beam area S is calculated by the following expression based on beam sizes a, b and the defect density referred to from step 2 (step S3). Since a beam shape is made to a rectangular shape here because the array probe is used, the beam sizes a, b show the lengths of the respective sides of a rectangle.

$$S = a \cdot b \cdot dp \quad (1)$$

where, a, b show beam sizes in a thickness direction and in a longer direction, and dp shows a defect density.

Next, the size of an artificial defect used in the sensitivity calibration may be input from the process computer, an input terminal, and the like (or when the artificial defect is the same at all times, the size thereof may be stored to the sensitivity calibration unit 70 without being input), and the difference (ratio) of intensity between the echo height of the size of the artificial defect and the echo height of an equivalent defect diameter corresponding to the total in-beam area S determined at step S3 is calculated.

Specifically the acoustic reflectivity R1 of, for example, a circular plane flaw can be shown by the following expression. When acoustic reflectivity in a scattering type penetrator is determined, Expression (2) calculates it using the equivalent defect diameter.

$$R1 = (2\pi r^2)/(\lambda x) = (2S)/(\lambda x) \quad (2)$$

where, r shows the radius of an equivalent defect (circular defect of the total in-beam area), λ shows a wavelength, and x shows a distance from a defect.

Further, a drilled hole ordinarily used in an artificial defect may be considered as a columnar flaw, and the acoustic reflectivity R2 of the columnar flaw can be shown by the following expression.

$$R2 = \sqrt{\{r/(r+x)\}} \quad (3)$$

Accordingly, the difference ΔG of signal intensity between the equivalent defect and the drilled hole can be determined by the following expression from R1, R2.

$$\Delta G = 20 * \log(R1/R2) \text{ (dB)} \quad (4)$$

Then, a sensitivity correction is performed based on ΔG determined at step S4 so that an obtained echo height is within a range in which it can be accurately processed and determined when a signal is processed as well as a threshold value is determined to determine a defect. When, for example, difference ΔG of signal intensity=−30 dB is determined and when the strength of a drilled hole DH is set to 100% on a chart (set to the maximum value of a dynamic range in a signal processing), since −30 dB is 3.1% of the maximum value of the dynamic range, it can not be recognized on the chart (in the signal processing) because it is excessively low. That is, resolution for determination is lowered and set to a level which is insufficient for determination by a signal. To cope with the above problem, when a sensitivity correction of, for example, 20 dB (10 times) and the like is performed, since the threshold value is set to 31%, it can be accurately determined on the chart as well as by the calculation of the signal processing. It is preferable to set the threshold value to the range of 20-60%, and it is sufficient to determine a sensitivity correction amount based on the difference ΔG of signal intensity so that it is within the range.

Further, when a sensitivity correction value is automatically determined, a threshold value may be previously set (to, for example, 50% and the like) and the sensitivity correction value may be determined from the ratio of the value of ΔG and the threshold value so that the value of ΔG is set to the threshold value.

Thereafter, a steel pipe for calibration having an artificial defect (for example, a 1.6 mmφ drilled hole) is inspected, and the sensitivity of an amplifier (not shown) of a received signal unit is adjusted so that the level of a received signal is set to a predetermined level (step S6). Further, the signal level used here is subjected to the same signal processing as that of an index value used to determine a defect in an ordinary flaw detection. Note that the predetermined level is preferably set to a value corresponding to 100% on a chart or to the maximum value of a dynamic range in a signal processing device. Note that an artificial defect for calibration may be inspected off-line by providing a mechanism capable of moving the ultrasonic flaw detection apparatus off-line or a steel pipe for calibration may be inspected similarly to an ordinary inspection in a manufacturing line.

Further, the sensitivity correction amount set at step S5 is set to the amplifier (step S7) as well as the threshold value determined at step S5 is set to the detection threshold value input unit (step S8). Thereafter, the threshold value is set to the defect determination unit, and it is determined by threshold value whether or not the required specifications are satisfied.

Note that the calibration can be also applied to a periodical calibration when the amplifier is varied as a time passes in addition to a timing at which inspection conditions are changed.

A quality control can be accurately performed by the calibration method described above even if a scattering type penetrator exists.

Example 2

Figure 29:
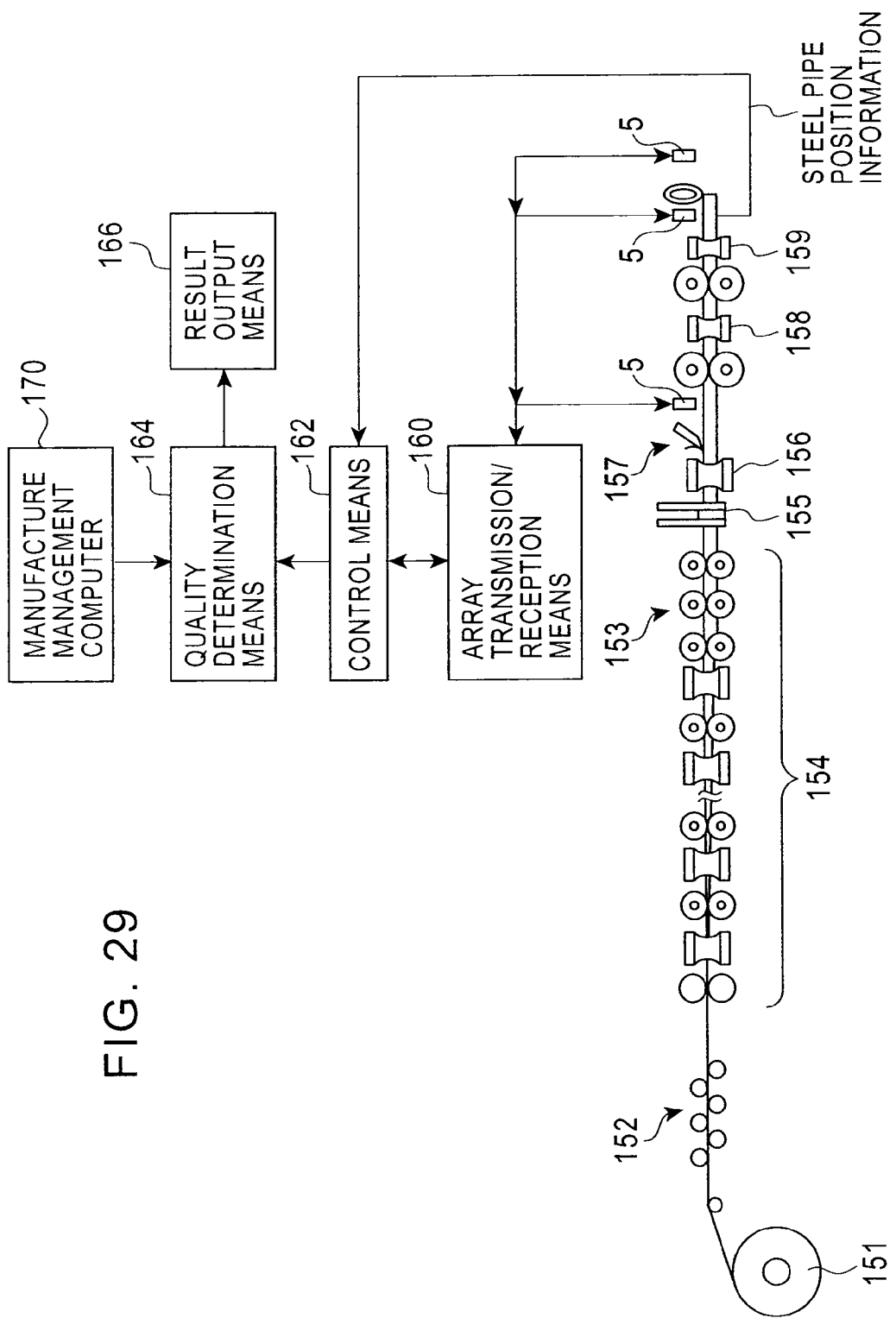
FIG. 29 is a view explaining an example 2 of the present invention.

Next, an arrangement example for applying the ultrasonic flaw detection method shown in the example 1 to a manufacturing process of a electric resistance welded steel pipe will be explained using FIG. 29. In FIG. 29, an apparatus has an uncoiler 151 for supplying a strip, a leveler 152 for correcting a shape, a roll forming unit 154, a fin path forming unit 155, an induction heater 156, a squeeze roll 157, and sizer 158. For example, a strip having a strip width of 1920 mm×strip thickness of 19.1 mm are welded by electric resistance welding and pass through the sizer 158 and A 600φ steel pipe are manufactured. In FIG. 29, 159 denotes a pipe cutter.

Here, a quality control can be performed by disposing the array probe 5 for the tandem flaw detection on, for example, the inlet side or the outlet side of the sizer 158 after the completion of welding or on the outlet side of the pipe cutter 159 and evaluating mechanical characteristics based of the result. Included in the arrangement are an array transmission/reception means 160 for performing transmission and reception of the array probe 5, a control means 162 for controlling respective conditions such as a beam width, an aperture width, an incident angle on a steel pipe, and the like in the transmission from and the reception to the array probe 5, a quality determination means 164 including a sensitivity calibration unit for determining a defect in a welded portion and evaluating mechanical characteristics based on the signal received by the array probe 5, and a result output unit 166 for displaying and printing a result of determination in the quality determination means 164. Note that, when the above means are caused to correspond to respecting function units of FIG. 28, the array transmission/reception means 160 includes an array transmission unit 36, an array reception unit 37, an array transmission law storage unit 34, and an array reception law storage unit 35, the control means 162 includes an aperture width controller 32, a gate position storage unit 33, a gate unit 38, a specimen size input unit 30, and an array probe storage unit 31, the quality determination means 164 includes a received signal storage unit 56, a signal processing unit 58, a sensitivity calibration unit 70, a parameter input means 60, a detection threshold value input unit 39, and index value/mechanical characteristics corresponding data 64.

Accordingly, when the quality control of a electric resistance welded steel pipe is performed by an ultrasonic flaw detection using the tandem method in a manufacturing line, a calibration can be performed by receiving an instruction for calibration from a manufacture management computer each time required specifications are changed or at a periodical timing and measuring calibration samples. Further, it is sufficient to perform a calibration method by the same procedure as that shown in the example 1.

Note that, when received signal data is stored to the received signal storage unit shown in FIG. 28, it is sufficient that, as to a flaw detection position in a pipe thickness direction, data is input from the control means 162 because a scan is performed by controlling transducers of an array probe, and, as to a flaw detection position in a pipe axis direction, data is input from a sensor and the like for detecting a moving distance of a steel pipe in a manufacturing line. As to conditions of the size and the like of the steel pipe, it is sufficient to input data by connecting the manufacture management computer 170 to the quality determination means 164 (or the control means 162). Further, when it is necessary to change the other inspection conditions depending on a type of a steel pipe, it is sufficient to input them from the manufacture management computer 170.

Example 3

Although the examples 1 and 2 explain examples for performing the sensitivity calibration to the steel pipe itself, since a similar calibration method can be performed even when a C-scan method is used although a steel pipe itself is not used, this method will be explained below.

Figure 30:
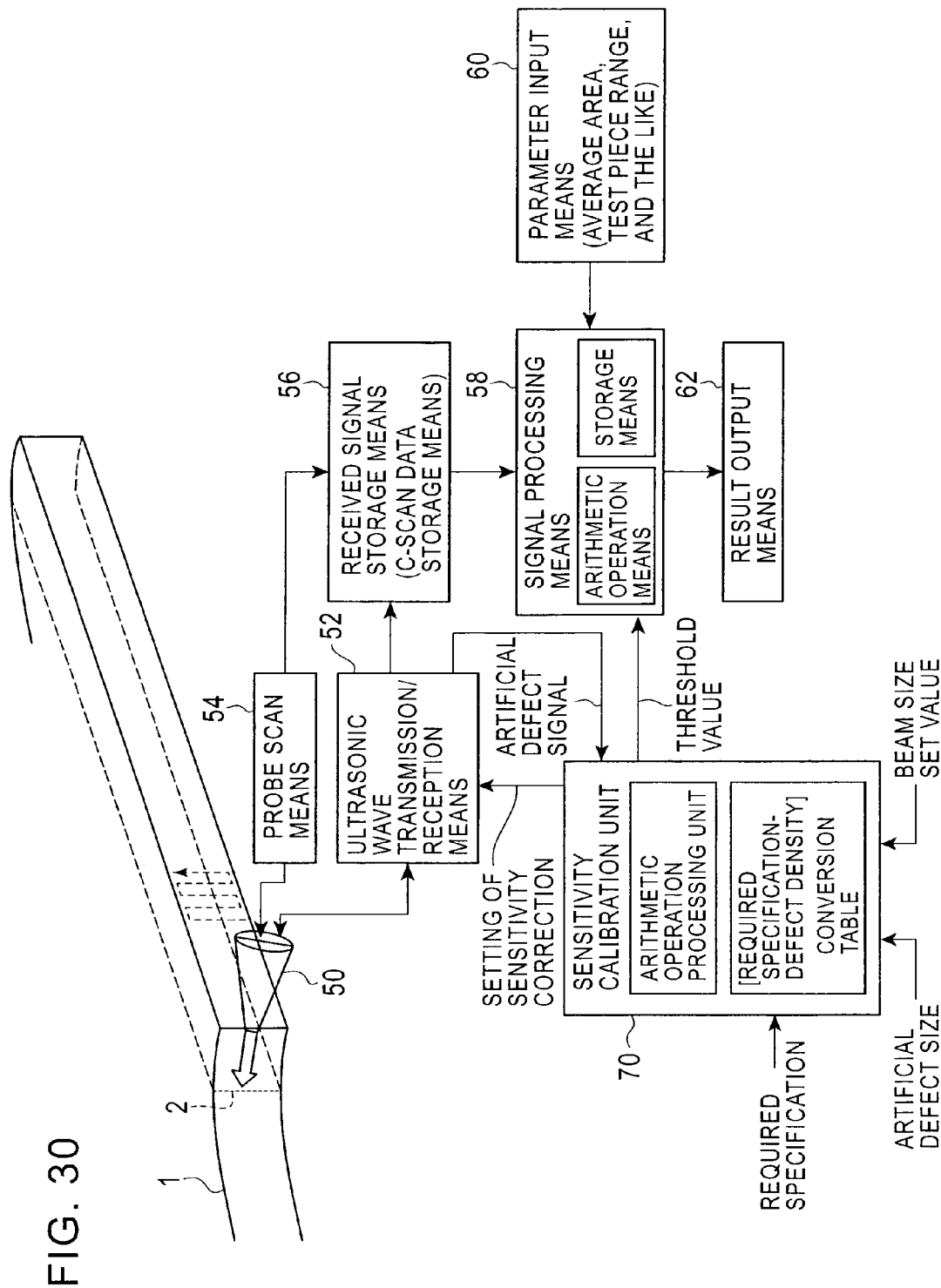
FIG. 30 is a view explaining an example 3 of the present invention.

FIG. 30 shows an example of an arrangement for performing the C-scan method. The example is composed of a probe 50 for performing an ultrasonic flaw detection by transmitting and receiving an ultrasonic wave to and from a cut-out welded surface, an ultrasonic wave transmission/reception means 52 for controlling the transmission and reception of an ultrasonic wave in the probe 50, a probe scan means 54 for sequentially scanning the probe in a pipe axis direction and in a pipe thickness direction to subject a welded surface of the cut-out sample to a C-scan, a received signal storage means 56 for storing C-scan data, a signal processing means 58 for subjecting the C-scan data to an arithmetic processing, a parameter input means 60 for inputting parameters necessary to the arithmetic processing, and a result output means 62, and a sensitivity calibration unit 70.

The received signal storage means 56 is arranged such that it stores the signal received by the ultrasonic wave probe 50 after the signal is caused to correspond to a position at which the welded surface is scanned by the probe scan means 54.

The received signal storage means 56 is, for example, a memory (two-dimensional memory) capable of storing received signal intensity with respect to a pipe axis direction and a pipe thickness direction and is a so-called C-scan data memory means having a function of storing the C-scan data.

The signal processing means 58 inputs parameters necessary to the arithmetic processing to be described later to the data of the memory by the parameter input means 60 and calculates index values having correlation with the mechanical characteristics, and the index values are displayed by images or printed to the result output means 62 such as a CRT, a liquid crystal monitor, a printer, and the like.

The sensitivity calibration unit 70 has an arithmetic processing unit and table data for deriving a defect density corresponding to the required specifications. The sensitivity calibration unit 70 is connected to the ultrasonic wave transmission/reception means 52 so that an artificial defect signal can be input from the ultrasonic wave transmission/reception means 52 thereto, and the sensitivity calibration unit 70 can set or input required specification, an artificial defect size, and an ultrasonic beam size. Further, a sensitivity correction value calculated by the sensitivity calibration unit 70 can be set to the ultrasonic wave transmission/reception means and a defect detection threshold value can be set to the signal processing unit.

A sample is made by being cut out (sliced) at a position of, for example, 8 mm from a welded surface (seam) using the above arrangement and is measured using the point focusing type probe 50 from an end surface with a beam width set to 440 μm on the welded surface at a frequency of 20 MHz so that a scattering type penetrator can be detected.

Figure 16:
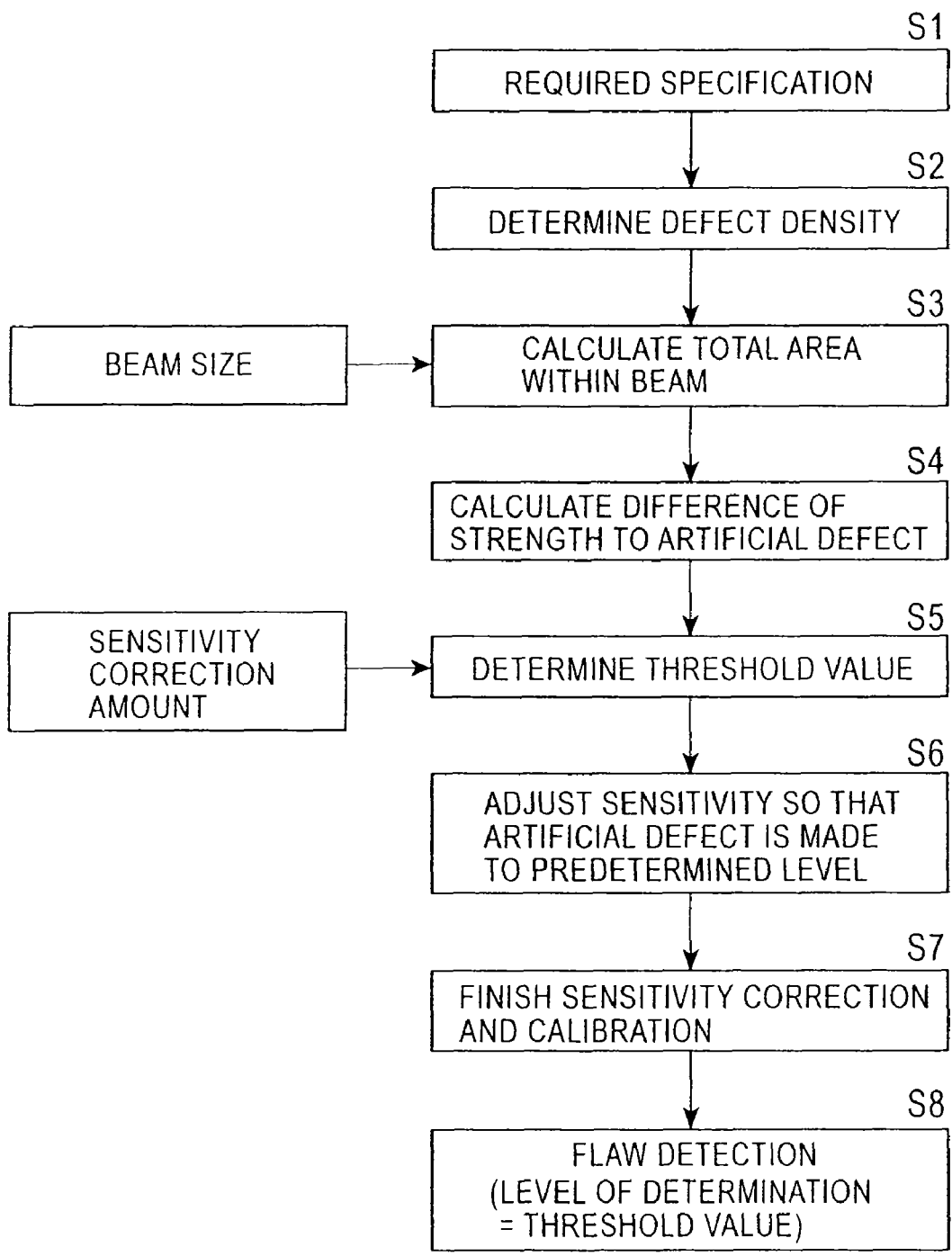
FIG. 16 is a flowchart of a sensitivity calibration procedure according to an embodiment of the invention.
Figure 17:
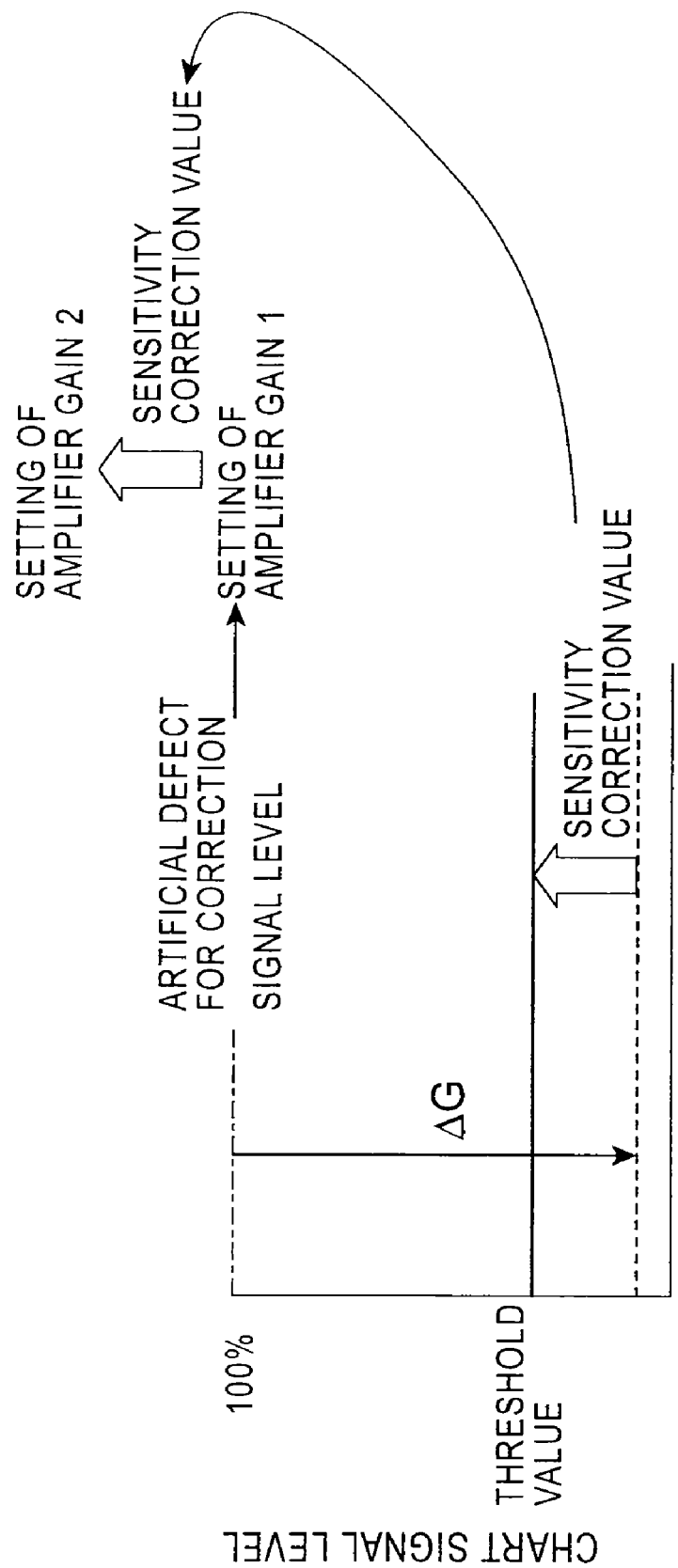
FIG. 17 is a view explaining how a threshold value of an embodiment of the present invention is set.

Since it is sufficient to perform the calibration according to the present invention by the sensitivity calibration unit 70 using the procedure of FIG. 16 likewise the tandem flaw detection of the example 1, the detailed explanation of the calibration is omitted. Note that, in the tandem flaw detection, although a defect density and a defect diameter are calculated from the required specifications based on the data shown in FIG. 15, a result is different from that of FIG. 15 because the measurement conditions of the C-scan method are different from those of the tandem flaw detection. Thus, it is sufficient to calculate data corresponding to FIG. 15 from FIGS. 9 and 10 described above. Further, since a beam shape is made to a circular shape and an oval shape, an equivalent defect diameter is calculated in accordance with them.

Note that, in the C-scan, since a beam is directly incident on the welded surface vertically, the aperture width D of a transducer for obtaining a beam width d is determined from the following expression.

$$D = \lambda(F/d) \quad (6)$$

where d shows a beam size at a flaw detection position, F shows a focal length, and λ shows a wavelength as shown in FIG. 19.

The invention claimed is:
1. A calibration method for an ultrasonic flaw detector, wherein the method comprises:
   obtaining a first signal intensity of the ultrasonic detector that is indicative of an artificial defect that is detected by an ultrasonic beam;
   utilizing the ultrasonic detector on a welded portion of a pipe body;
   calculating a second signal intensity of the ultrasonic detector based on a total area of defects existing in a region of an ultrasonic beam on a welded surface; and determining a defect detection threshold value for the ultrasonic detector based on a signal intensity difference between the first and second signal intensities.

2. The calibration method of claim 1, wherein the total area of the defects is determined from a defect density, which is determined from a desired quality level on the welded surface of the welded portion of the pipe body in a pipe axis direction and an area of the ultrasonic beam on the welded surface.

3. The calibration method of claim 2, wherein a relation between the defect density and the quality level is previously determined by a Charpy impact test.

4. The calibration method of claim 2, wherein the signal intensity difference between the first and second signal intensities is determined based on a relative relation of acoustic reflectivity.

5. A method for performing quality control of a pipe body by using an ultrasonic flaw detector on a welded portion of the pipe body in at least a pipe axis direction, the method comprising:
   determining a defect detection threshold value by the calibration method of claim 1.

6. The quality control method of claim 5, further comprising:
   transmitting from a wave transmission unit an ultrasonic wave to a welded surface of a welded portion of the pipe body in a pipe axis direction; and
   partly or entirely receiving in a wave reception unit a reflected wave from the welded surface,
   wherein the wave transmission unit and the wave reception unit perform ultrasonic flaw detection using an ultrasonic flaw detection apparatus comprising a transmission/reception unit composed of different transducer groups on one, two, or more array probes disposed in a pipe peripheral direction.

7. The quality control method of claim 6, further comprising:
   transmitting ultrasonic waves from the wave transmission unit to the welded surface of the welded portion of the pipe body in the pipe axis direction and to an inner surface of the pipe body so that the ultrasonic waves are incident thereon in a range of from 33.2° to 56.8°, respectively; and
   partly or entirely receiving in the wave reception unit a reflected wave reflected in a range of from −12° to 16° with respect to a normal reflection direction on the welded surface.

8. The quality control method of claim 7, wherein a beam width of the ultrasonic waves on the welded surface is set within a range of from 0.5 mm to 2.5 mm.

9. A method of manufacturing a pipe body, comprising:
   manufacturing a pipe body; and
   performing a quality control of the pipe body by the quality control method of claim 5.

* * * * *